United States Patent
Yamasaki et al.

(10) Patent No.: US 9,297,823 B2
(45) Date of Patent: *Mar. 29, 2016

(54) SPECIMEN TRANSPORTER AND SPECIMEN IMAGING SYSTEM

(71) Applicant: Sysmex Corporation, Kobe-shi, Hyogo (JP)

(72) Inventors: Mitsuo Yamasaki, Kobe (JP); Hidetaka Hayama, Kobe (JP); Yuichiro Ohmae, Kobe (JP); Tomoyuki Asahara, Kobe (JP); Takaaki Nagai, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 93 days.

This patent is subject to a terminal disclaimer.

(21) Appl. No.: 14/032,519

(22) Filed: Sep. 20, 2013

(65) Prior Publication Data

US 2014/0093423 A1      Apr. 3, 2014

(30) Foreign Application Priority Data

Sep. 28, 2012   (JP) ................................. 2012-215795

(51) Int. Cl.
| | |
|---|---|
| *G01N 35/10* | (2006.01) |
| *G01N 35/00* | (2006.01) |
| *G01N 35/04* | (2006.01) |
| *G01N 35/02* | (2006.01) |

(52) U.S. Cl.
CPC ...... *G01N 35/1081* (2013.01); *G01N 35/00029* (2013.01); *G01N 35/04* (2013.01); *G01N 35/026* (2013.01); *G01N 2035/00039* (2013.01); *G01N 2035/00138* (2013.01)

(58) Field of Classification Search
None
See application file for complete search history.

(56) References Cited

U.S. PATENT DOCUMENTS

| | | | |
|---|---|---|---|
| 4,501,495 A | 2/1985 | Faulkner et al. | |
| 6,847,481 B1* | 1/2005 | Ludl et al. | 359/391 |
| 2003/0003022 A1 | 1/2003 | Tamura et al. | |
| 2005/0186114 A1* | 8/2005 | Reinhardt et al. | 422/65 |
| 2005/0191670 A1 | 9/2005 | Stylli et al. | |
| 2006/0029519 A1* | 2/2006 | Nakaya et al. | 422/63 |
| 2006/0120921 A1* | 6/2006 | Elliot et al. | 422/63 |
| 2006/0193754 A1 | 8/2006 | Toyoda et al. | |

(Continued)

FOREIGN PATENT DOCUMENTS

| | | |
|---|---|---|
| JP | 07-260649 A | 10/1995 |
| JP | 2008-139063 A | 6/2008 |
| JP | 4850825 B2 | 1/2012 |

OTHER PUBLICATIONS

Non-Final Rejection issued in co-pending U.S. Appl. No. 14/038,102 on Jun. 4, 2015, 58 pages.

*Primary Examiner* — Jill Warden
*Assistant Examiner* — Benjamin Whatley
(74) *Attorney, Agent, or Firm* — Brinks Gilson & Lione

(57) ABSTRACT

A specimen transporter connected to a specimen imaging apparatus, the specimen transporter including a specimen receiving section that receives a specimen plate and a specimen storage section that stores an imaged specimen plate. Specimen transporting sections transport the specimen plate from the specimen receiving section to the specimen imaging apparatus and from the specimen imaging apparatus to the specimen storage section. A control section controls operations of the specimen transporting sections to transport the specimen plate received by the specimen receiving section to the specimen imaging apparatus and transport the imaged specimen plate received from the specimen imaging apparatus to the specimen storage section.

18 Claims, 23 Drawing Sheets

(56) References Cited

U.S. PATENT DOCUMENTS

| | | |
|---|---|---|
| 2006/0210451 A1 | 9/2006 | Anderson et al. |
| 2007/0057106 A1* | 3/2007 | Scampini ............... 242/336 |
| 2007/0076190 A1 | 4/2007 | Nakaya et al. |
| 2007/0077550 A1 | 4/2007 | Tohma et al. |
| 2007/0128073 A1 | 6/2007 | Tappen |
| 2007/0148046 A1* | 6/2007 | Nakaya ................ 422/82.05 |
| 2007/0172396 A1* | 7/2007 | Neeper et al. ............ 422/104 |
| 2007/0205126 A1* | 9/2007 | Elsener et al. ........... 206/456 |
| 2008/0014119 A1* | 1/2008 | Metzner ................... 422/65 |
| 2008/0028835 A1* | 2/2008 | Higuchi ................. 73/53.01 |
| 2008/0201082 A1* | 8/2008 | Tohma et al. ............. 702/19 |
| 2009/0087904 A1* | 4/2009 | Heid et al. ............. 435/307.1 |
| 2009/0280572 A1 | 11/2009 | Ribeiro et al. |
| 2010/0028124 A1 | 2/2010 | Lackner et al. |
| 2010/0083772 A1 | 4/2010 | Tanaka |
| 2010/0111384 A1 | 5/2010 | Nagal et al. |
| 2010/0166606 A1 | 7/2010 | Koike et al. |
| 2010/0229702 A1* | 9/2010 | Fujimoto ............... G01N 1/06 83/23 |
| 2010/0248292 A1 | 9/2010 | Kuwano et al. |
| 2010/0324722 A1 | 12/2010 | Fritchie et al. |
| 2011/0136135 A1* | 6/2011 | Larsen et al. ............. 435/7.1 |
| 2011/0304722 A1* | 12/2011 | Nilsson et al. ............ 348/79 |
| 2012/0003065 A1* | 1/2012 | Hirono ................. G02B 21/26 414/222.02 |
| 2012/0060539 A1* | 3/2012 | Hunt et al. ............... 62/336 |
| 2012/0064638 A1 | 3/2012 | Onomichi et al. |
| 2012/0163680 A1* | 6/2012 | Lefebvre ................. 382/128 |
| 2013/0020175 A1* | 1/2013 | McKeen et al. .......... 198/346.1 |
| 2013/0239665 A1* | 9/2013 | Loppacher et al. ........ 73/61.59 |
| 2014/0092382 A1* | 4/2014 | Hayama ................. 356/244 |
| 2014/0093423 A1 | 4/2014 | Yamasaki et al. |
| 2014/0093424 A1 | 4/2014 | Asahara |
| 2014/0178169 A1 | 6/2014 | Herbert et al. |
| 2014/0273088 A1* | 9/2014 | Winther ................ 435/40.52 |

* cited by examiner

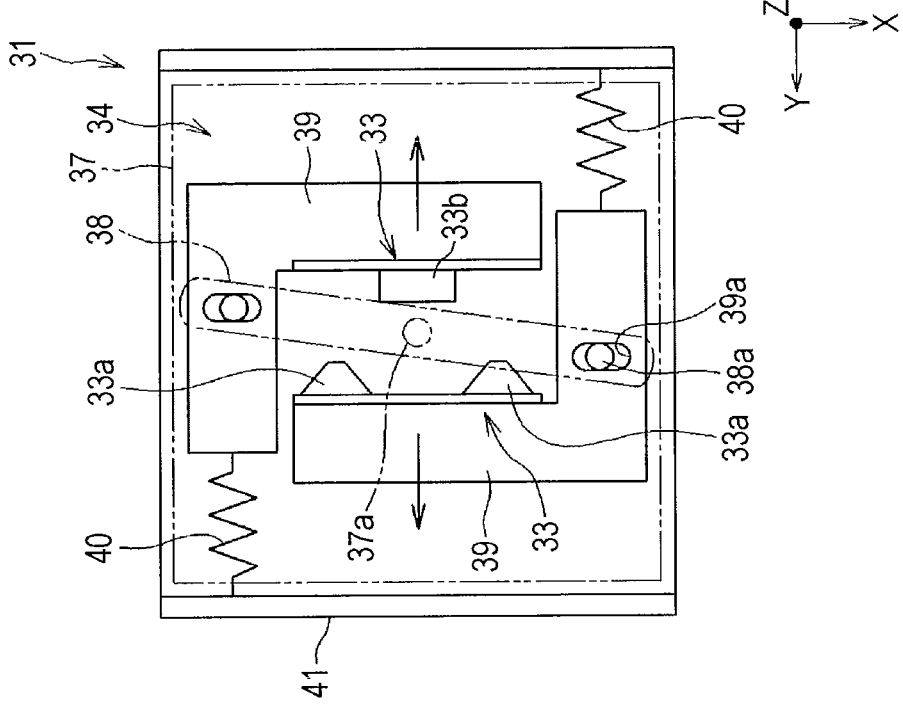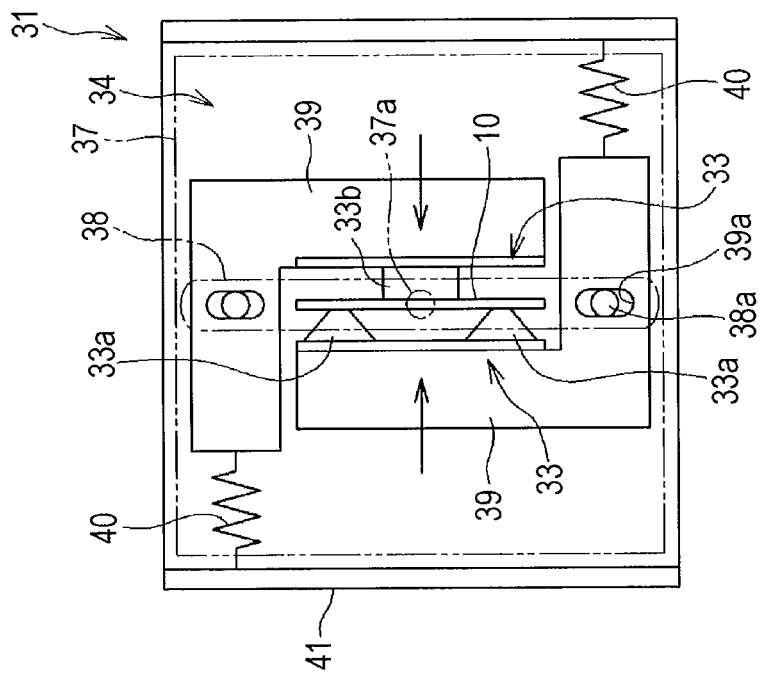

SPECIMEN TRANSPORTER AND SPECIMEN IMAGING SYSTEM

RELATED APPLICATIONS

This application claims priority under 35 U.S.C. §119 to Japanese Patent Application No. 2012-215795 filed on Sep. 28, 2012, the entire content of which is hereby incorporated by reference.

BACKGROUND OF THE INVENTION

1. Technical Field Text

The present invention relates to a specimen transporter capable of performing transportation of specimen plates to a specimen imaging apparatus and collecting of imaged specimen plates from the specimen imaging apparatus, and a specimen imaging system equipped with the same.

2. Background Information

An imaging apparatus for imaging a specimen, which is prepared by smearing a sample such as blood on a slide glass and performing staining processing, and the like, with a microscope and a camera is conventionally known. An image imaged by the imaging apparatus is used for automatic cell classification, and manual cell classification by an operator.

In this type of specimen imaging apparatus, the supplied specimen is automatically transported to the microscope, and automatically collected to a predetermined collecting location after being performed with imaging by the camera. For example, in the specimen imaging apparatus disclosed in U.S. Patent Application Publication No. 2011/304722, after a magazine stored with a specimen is installed in a cavity, a handling device grips the specimen and takes out the specimen from the magazine, and then transports the specimen to an optical system including the microscope, and the like. The specimen, which image is imaged in the optical system, is again returned to the magazine by the handling device.

U.S. Patent Application Publication No. 2008/201082 discloses a specimen image imaging system capable of carrying out a series of operations from preparing to analyzing the specimens. Specifically, the specimen image imaging system prepares a specimen of blood with the specimen preparing apparatus, transports the specimen to a specimen imaging apparatus (blood image analyzer) with a specimen transporter, images the specimen in the specimen imaging apparatus, and thereafter collects the specimen in a predetermined magazine. In such specimen image imaging system, the collecting of the specimen to the magazine is carried out in the specimen imaging apparatus.

The specimen imaging apparatuses described in U.S. Patent Application Publication No. 2011/304722 and U.S. Patent Application Publication No. 2008/201082 both interiorly include a mechanism for collecting the imaged specimen in the magazine.

Such specimen imaging apparatus is required to have a configuration of simply discharging the imaged specimen to the outside for miniaturization, simplification, and the like, and the subsequent collecting of the specimen is to be left to the external device.

However, when incorporating the specimen imaging apparatus that does not have a function of collecting specimens in the specimen imaging system, a device for storing the specimen in the magazine needs to be newly added, which increases the number of devices in the system as a whole and may possibly increase the system scale.

SUMMARY OF THE INVENTION

The scope of the present invention is defined solely by the appended claims, and is not affected to any degree by the statements within this summary.

A first aspect of the present invention is a specimen transporter used by being connected to a specimen imaging apparatus, the specimen transporter comprising a specimen receiving section configured to receive a specimen plate; a specimen storage section configured to store an imaged specimen plate; and a specimen transporting section configured to transport a specimen plate from the specimen receiving section to the specimen imaging apparatus and from the specimen imaging apparatus to the specimen storage section, wherein the specimen transporting section transports the specimen plate received by the specimen receiving section to the specimen imaging apparatus and transports the imaged specimen plate received from the specimen imaging apparatus to the specimen storage section.

A second aspect of the present invention is a specimen imaging system comprising a specimen preparing apparatus configured to prepare a specimen plate of a sample; a specimen imaging apparatus configured to image the specimen plate; and a specimen transporter configure to transport the specimen plate between the specimen preparing apparatus and the specimen imaging apparatus; wherein the specimen transporter comprises a specimen receiving section configured to receive the specimen plate prepared by the specimen preparing apparatus; a specimen storage section configured to store the specimen plate imaged by the specimen imaging apparatus; and a specimen transporting section configured to transport the specimen plate from the specimen receiving section to the specimen imaging apparatus and from the specimen imaging apparatus to the specimen storage section, wherein the specimen transporting section transports the specimen plate received by the specimen receiving section to the specimen imaging apparatus and transports the imaged specimen plate received from the specimen imaging apparatus to the specimen storage section.

BRIEF DESCRIPTION OF THE DRAWINGS

FIGS. 5A and 5B are schematic bottom views describing an opening/closing operation of a gripping nail;

DETAILED DESCRIPTION OF THE PREFERRED EMBODIMENTS

The preferred embodiments of the present invention will be described hereinafter with reference to the drawings.

[Schematic Configuration of Specimen Testing System]

Figure 1:
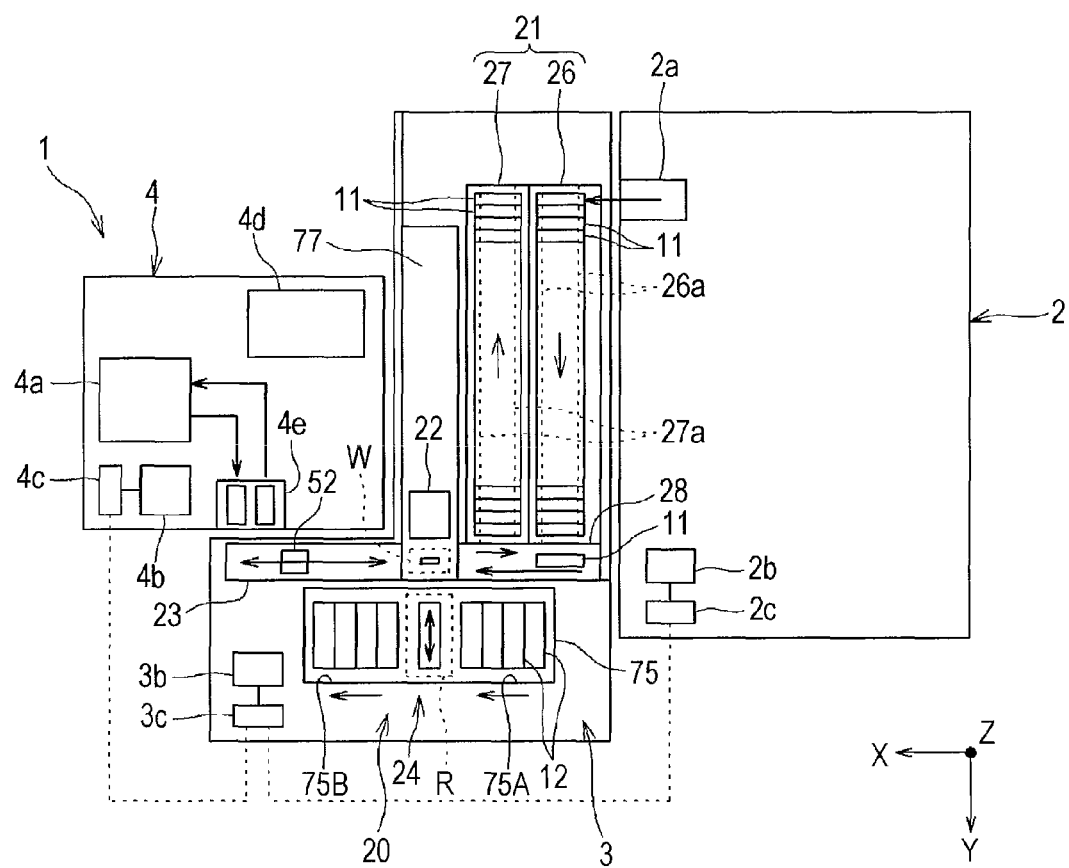
FIG. 1 is an overall configuration diagram showing a specimen testing system according to an embodiment of the present invention.

FIG. 1 is an overall configuration diagram showing a specimen testing system according to one embodiment of the present invention.

A specimen testing system 1 of the present embodiment is a system that is configured by a specimen preparing apparatus 2, a specimen transporter 3, and a specimen imaging apparatus (specimen testing apparatus) 4, and that automatically performs a series of operations from preparing the specimen of the sample such as blood up to imaging (testing, analyzing) of the specimen.

In the present specification, description will be made assuming the X direction shown in FIG. 1 as left-right direction, Y direction as front-back direction, and Z direction as up-down direction. In FIG. 1, the lower side is assumed as the front side and the upper side is assumed as the back side, the specimen preparing apparatus 2 is arranged at a right side portion of the specimen testing system 1, the specimen imaging apparatus 4 is arranged at a left side portion, and the specimen transporter 3 is arranged between the left and the right of the specimen preparing apparatus 2 and the specimen imaging apparatus 4. The specimen transporter 3 has one part arranged to overlap the front side of the specimen imaging apparatus 4. Furthermore, in the present specification, "lateral" is sometimes described to mean the left-right direction, and "longitudinal" is sometimes described to mean the front-back direction.

Figure 2:
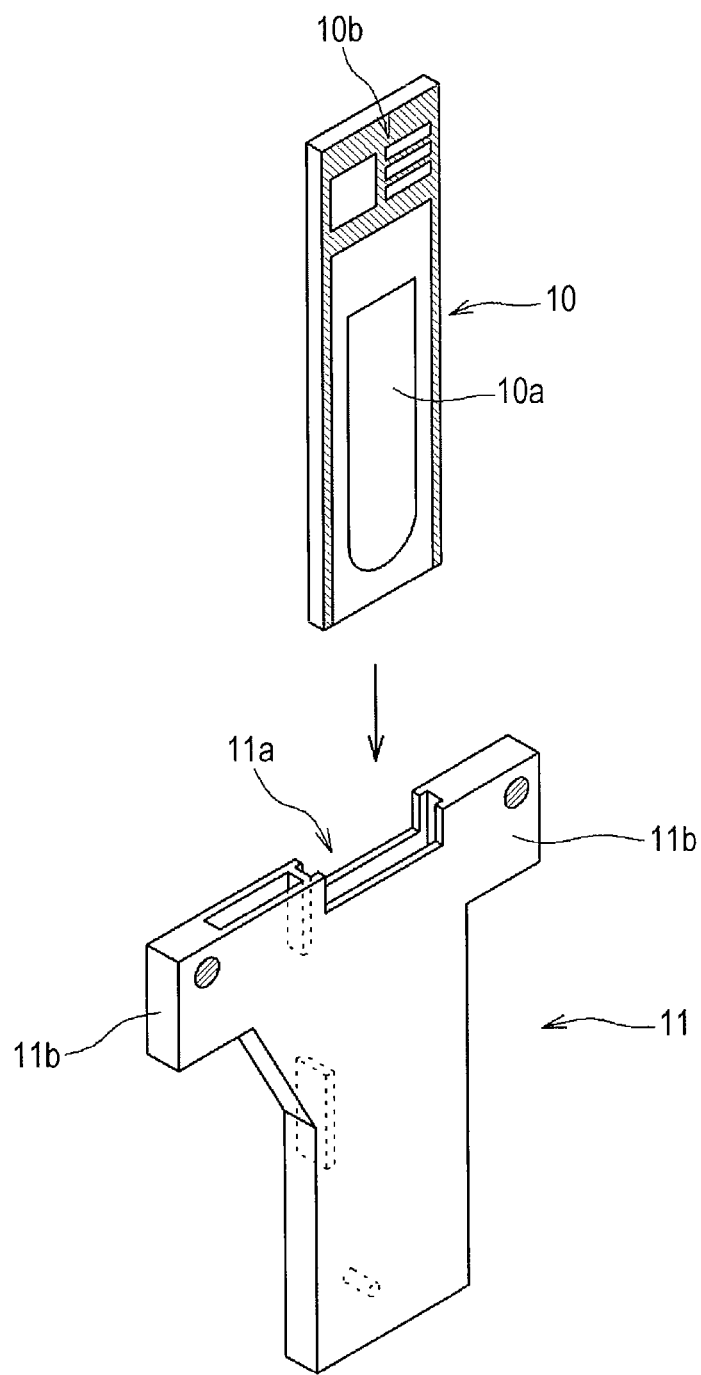
FIG. 2 is a perspective view of a specimen plate and a cassette.

The specimen preparing apparatus 2 smears blood, which is the sample, on a slide glass, and performs processing such as drying, staining, and the like to prepare a specimen plate (hereinafter also simply referred to as "specimen") 10. FIG. 2 is a perspective view of the specimen plate 10 and a cassette 11. The specimen plate 10 is made from a rectangular-shaped plate material such as glass, and the sample is smeared at a central portion 10a. Sample information (barcode indicating sample number, date, receipt number, name, information of sample, etc.) 10b is printed at an upper part of the specimen plate 10.

The prepared specimen plate 10 is supplied to the next specimen transporter 3 while being stored in the cassette 11. A cassette supplying section 2a for supplying the cassette 11 having the specimen plate 10 therein to the specimen transporter 3 is provided at a back part on the left side of the specimen preparing apparatus 2. The operation of each mechanism section in the specimen preparing apparatus 2 is controlled by a control section 2b. The control section 2b includes a CPU, a storage unit, and the like, and is communicably connected with other devices by way of a communication section 2c.

The cassette 11 storing the specimen plate 10 therein is a flat case formed to a substantially T-shape in front view. At a middle of an upper end portion of the cassette 11 is formed an insertion port 11a for inserting the specimen plate 10. The specimen plate 10 inserted to the insertion port 11a projects out from the cassette 11 so that the sample information 10b at the upper part is exposed to the outside. A collar section 11b is formed at the upper part of the cassette 11 so as to project out to both left and right sides.

The specimen transporter 3 has a function of transporting the specimen plate 10 (cassette 11) received from the specimen preparing apparatus 2 to the adjacent specimen imaging apparatus 4. Specifically, the specimen transporter 3 takes out the specimen plate 10 from the cassette 11 and transports the specimen plate 10 to the specimen imaging apparatus 4 through a predetermined path. The specimen transporter 3 also has a function of collecting the specimen plate 10 performed with imaging in the specimen imaging apparatus 4, and storing the specimen plate in a predetermined rack (collecting box) 12. The operation of each mechanism section (specimen storage device 20, specimen transport mechanisms 21 to 23, etc. described later) in the specimen transporter 3 is controlled by a control section 3b. The control section 3b includes a CPU, a storage unit, and the like and is connected to the control section 2b of the specimen preparing apparatus 2 by way of communication sections 3c, 2c, so that information can be transmitted and received to perform mutually cooperating operations. The detailed description of the specimen transporter 3 will be described later.

The specimen imaging apparatus 4 transports the specimen plate 10 received from the specimen transporter 3 to an imaging section 4a to image the sample in the imaging section 4a. The imaged image data is transmitted to a control section 4b. The control section 4b includes a CPU, a storage unit, and the like, and executes predetermined processing such as characteristic extraction processing, identification and classification processing, and the like of the cells based on the image data. The imaged image data and the analysis results may be displayed on a display monitor 4d or output through a printer or the like (not shown). The control section 4b is connected to the control section 3b of the specimen transporter 3 by way of communication sections 4c, 3c, so that information can be transmitted and received to perform mutually cooperating operations. The portion performing the processing related to analysis in the control section 4b of the specimen imaging apparatus 4 may be configured by a single control device such as a personal computer, and the like.

[Configuration of Specimen Transporter 3]

The specimen transporter 3 will be described in detail below.

As shown in FIG. 1, the specimen transporter 3 according to the present embodiment is roughly divided to specimen transport mechanisms 21 to 23, and the specimen storage device 20. The specimen transport mechanisms include a cassette transport mechanism 21, a vertical transport mechanism 22, and a horizontal transport mechanism 23.

The specimen storage device 20 is configured by a rack transport mechanism 24 and a rack accumulating section 75 (specimen storage section).

The specimen plate 10 is transported to the specimen imaging apparatus 4 by the specimen transport mechanisms 21 to 23, and delivered to the specimen imaging apparatus 4. The specimen plate 10 performed with imaging in the specimen imaging apparatus 4 is stored in a predetermined rack 12 by the horizontal transport mechanism 23, the vertical transport mechanism 22, and the rack transport mechanism 24, and the entire rack 12 can be collected thereafter from the specimen transporter 3.

[Configuration of Cassette Transport Mechanism 21]

The cassette transport mechanism 21 includes a specimen receiving section 26 for receiving and accumulating the cassette 11 having the specimen plate 10 therein supplied from the cassette supplying section 2a of the specimen preparing apparatus 2, a cassette collecting section 27 for collecting the cassette 11, from which the specimen plate 10 is taken out, and a lateral transport section 28 for transporting the cassette 11 in the left-right direction.

The specimen receiving section 26 can store a large number of cassettes 11 having the specimen plate 10 therein so as to be lined in the front-back direction. The specimen receiving section 26 can contain, for example, 90 cassettes 11. The specimen receiving section 26 includes a pair of left and right belt conveyors (longitudinal moving section) 26a extending in the front-back direction. The cassette 11 is held by placing the collar section 11b (see FIG. 2) on the left and right belt conveyors 26a, and is moved forward by sending the belt conveyor 26a. Since the specimen receiving section 26 can contain a plurality of specimen plates 10, the difference in the cycle of preparing the specimen plate 10 in the specimen preparing apparatus 2 (e.g., 120/hour) and the cycle of imaging in the specimen imaging apparatus 4 (e.g., 30/hour) can be absorbed.

The cassette collecting section 27 is arranged adjacent on the left side of the specimen receiving section 26, and can store a large number of cassettes 11, from which the specimen plate 10 is removed, so as to be lined in the front-back direction. 90 cassettes 11, which is the same number as the specimen receiving section 26, for example, can be stored in the cassette collecting section 27. The cassette collecting section 27 includes a pair of left and right belt conveyors (longitudinal transport section) 27a extending in the front-back direction. The cassette 11 is held by placing the collar section 11b (see FIG. 2) on the left and right belt conveyors 27a, and is moved backward by sending the belt conveyor 27a.

The lateral transport section 28 is arranged at the front end portion of the specimen receiving section 26 and the cassette collecting section 27. The lateral transport section 28 holds the cassette 11 at the front end of the specimen receiving section 26 and transports the same in the left-right direction. In the process of being transported in the left-right direction, the specimen plate 10 is taken out from the cassette 11, and the emptied cassette 11 is collected by the cassette collecting section 27.

Figure 3A:
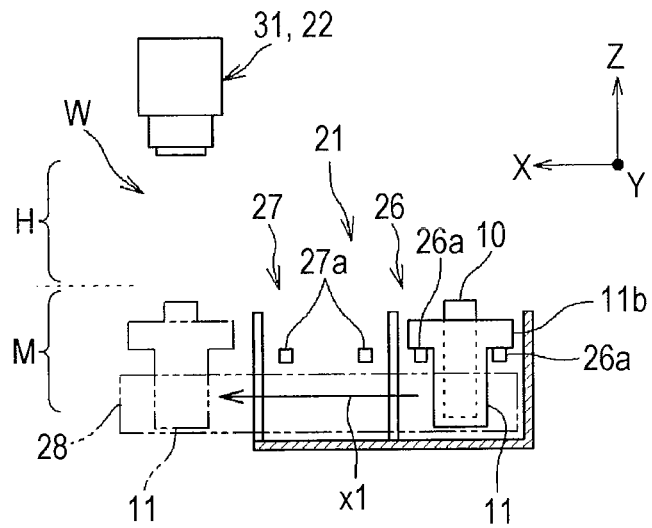
FIGS. 3A to 3C are front explanatory views showing operation of a cassette transport mechanism (lateral transport section) in a specimen transporter.
Figure 3B:
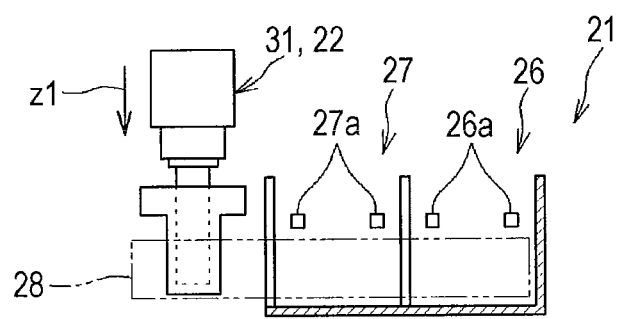
Figure 3C:
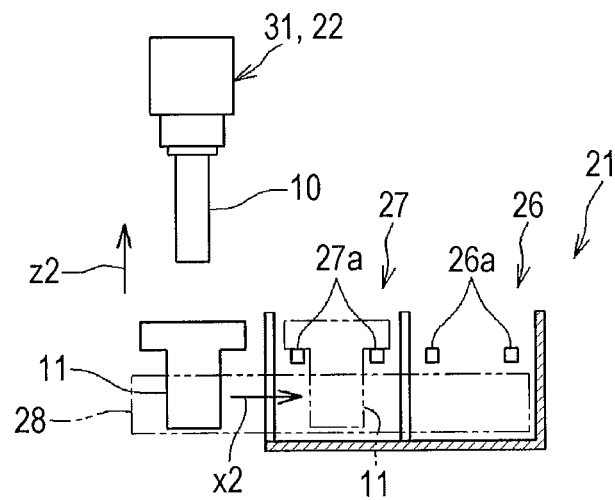

Specifically, as shown in FIGS. 3A to 3C, the lateral moving section 28 takes out and holds the cassette 11 at the front end of the specimen receiving section 26, and transports the same in the left direction (arrow x1) (see FIG. 3A). The cassette 11 is positioned at a predetermined specimen transfer position W (which is a position for receiving the specimen plate 10 from the vertical transport mechanism 22 and giving the specimen plate 10 to the vertical transport mechanism 22) set at the left side of the front end portion of the cassette transport mechanism 21. At such specimen transfer position W, a gripping section 31 of the vertical transport mechanism 22, to be described later, is waiting on the upper side (upper position H). The gripping section 31 moves to a middle position M on the lower side (arrow z1) to grip the specimen plate 10, and thereafter, returns to the upper side (arrow z2) to remove the specimen plate 10 from the cassette 11 (see FIGS. 3B, C).

The lateral transport section 28 also transports the cassette 11, from which the specimen plate 10 is removed, in the right direction (arrow x2), positions the same at the front end portion of the cassette collecting section 27, and transfers the cassette 11 to the front end portion of the cassette collecting section 27. The cassette collecting section 27 moves the transferred emptied cassette 11 toward the back side with the belt conveyor, and waits until the next reception. The lateral transport section 28 again receives the next cassette 11 from the specimen receiving section 26, and repeatedly performs the operations described above.

The cassette transport mechanism 21 of the present embodiment transports the cassette 11 in a standing posture in all of the specimen receiving section 26, the lateral transport section 28, and the cassette collecting section 27. A complex mechanism for changing the posture of the cassette 11 is thus not necessary, and the structure can be simplified.

As a mode of holding the cassette 11 with the lateral transport section 28, various modes such as a mode of supporting the lower surface or the collar section 11b of the cassette 11 from below, a mode of sandwiching the cassette 11 with a clamp member, and the like, a mode of suctioning with a suction disc, and the like may be adopted. A winding transportation mechanism such as the belt conveyor, chain, and the like, and an expansion/contraction operation mechanism such as a fluid pressure cylinder and the like, can be adopted to transport the held cassette 11 in the left-right direction.

[Configuration of Vertical Transport Mechanism 22]

Figure 4:
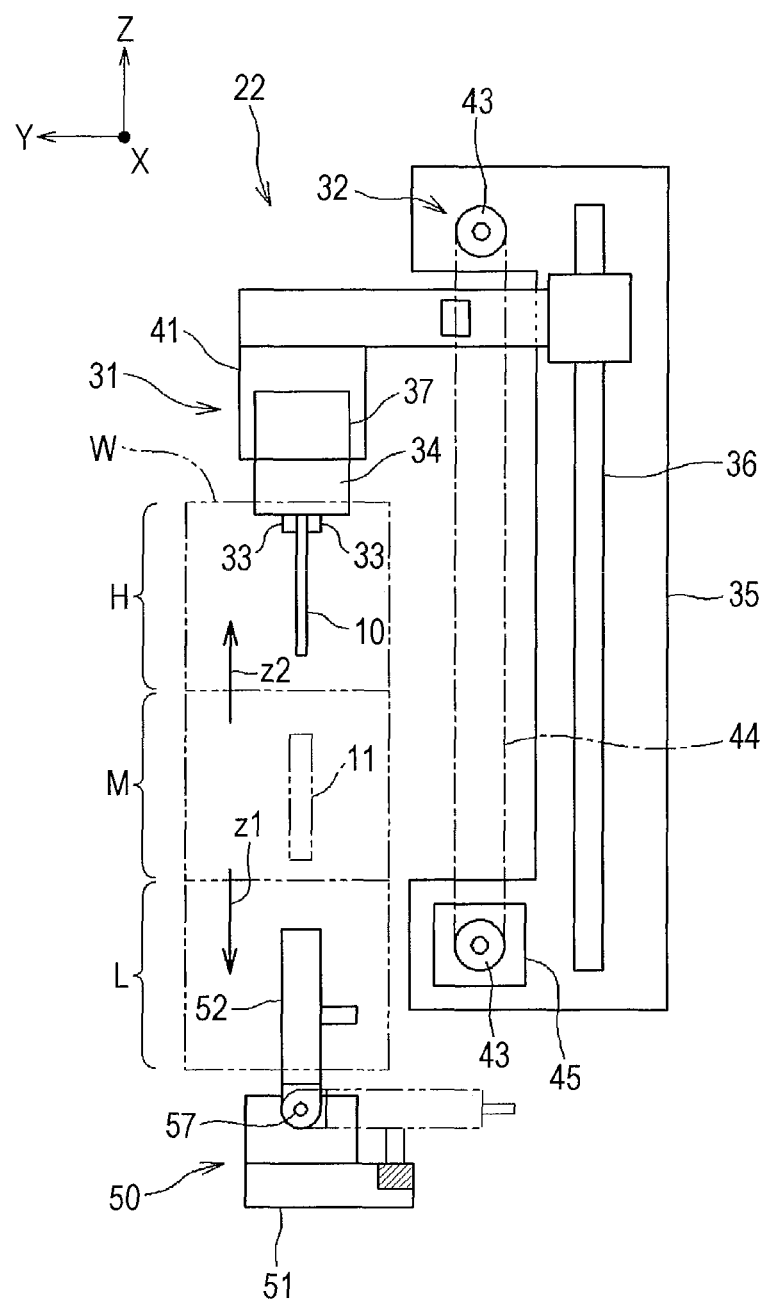
FIG. 4 is a schematic side view showing a vertical transport mechanism in the specimen transporter.

FIG. 4 is a schematic side view showing the vertical transport mechanism 22 in the specimen transporter 3.

The vertical transport mechanism 22 includes the gripping section (holder) 31 for gripping the specimen plate 10, and the up-down moving section 32 for raising and lowering the gripping section 31 up and down. The gripping section 31 includes a pair of front and back gripping nails 33, and an open/close mechanism 34 for opening/closing the gripping nails 33 forward and backward. The gripping (holding) and the releasing of the specimen plate 10 can be carried out by opening/closing the gripping nails 33 forward and backward. The gripping section 31 is supported to be movable in the up-down direction by a supporting frame 35 of the vertical transport mechanism 22. The supporting frame 35 includes a guide rail 36 that extends in the up-down direction and that guides the up-down movement of the gripping section 31.

FIGS. 5A and 5B are schematic bottom views describing the opening/closing operation of the gripping nails 33, FIG. 5A shows a state in which the gripping nails 33 are closed and FIG. 5B shows a state in which the gripping nails 33 are opened. One gripping nail 33 includes two projections 33a arranged side by side on the left and the right. The other gripping nail 33 includes one projection 33b at a position corresponding to between the two projections 33a. The gripping nails 33 thus sandwich and grip the specimen plate 10 at three points with the three projections 33a, 33b. The projections 33a, 33b are made from an elastic material such as rubber. The projection 33a of one gripping nail 33 is formed to a cone shape, and the projection of the other gripping nail 33 is formed to a cuboid shape or a cubic shape. The contacting surface with respect to the specimen plate 10 can be reduced by forming the projection 33a to a cone shape, thus enhancing the gripping pressure.

The open/close mechanism 34 includes a drive motor 37, an operation rod 38 coupled to an output shaft 37a of the drive motor 37, a pair of operation members 39 coupled to each end of the operation rod 38 by way of a pin 38a, and a biasing member 40 including a tension coil spring. The drive motor 37 is fixed to a fixing frame 41 of the gripping section 31. The operation member 39 is coupled to the pair of gripping nails 33, and is supported by the fixing frame 41 in a state movable in the front-back direction with the gripping nails 33. A long hole 39a, which is long in the left-right direction, is formed in the operation member 39, and the pin 38a is engaged with the long hole 39a. The biasing member 40 biases the gripping nail 33 on the front side and the operation member 39 backward, and biases the gripping nail 33 on the back side and the operation member 39 forward.

Therefore, the pair of gripping nails 33 are biased in a direction of approaching each other by the biasing member 40, and the specimen plate 10 can be gripped by the biasing force. When the operation rod 38 is turned by the drive motor 37, the pair of gripping nails 33 and the operation member 39 move in a direction of separating from each other, thus opening the pair of gripping nails 33. Thus, if the specimen plate 10 is gripped by the biasing force of the biasing member 40, the specimen plate 10 can be continuously gripped without being dropped even if current flow to the drive motor 37 is stopped while gripping the specimen plate 10.

As shown in FIG. 4, the up-down moving section 32 includes a belt conveyor extending in the up-down direction, which belt conveyor includes a pair of upper and lower pulleys 43 arranged on the supporting frame 35, a belt 44 wound around the pulleys 43, and a drive motor 45 for rotatably driving one pulley 43. The gripping section 31 is coupled to the belt 44. The gripping section 31 can be moved in the up-down direction by sending the belt 44 with the drive motor 45. The up-down moving section 32 is not limited to the belt conveyor, and other configurations such as the chain transportation mechanism, the expansion/contraction operation mechanism including the fluid pressure cylinder, and the like may be adopted.

The vertical transport mechanism 22 transports the specimen plate 10 gripped by the gripping section 31 in the up-down direction at the specimen transfer position W described above, and positions the specimen plate 10 to at least three heights, the upper position H, the middle position M, and the lower position L. The cassette transport mechanism 21 described above is arranged at the middle position M, the specimen plate 10 is removed from the cassette 11 by moving to the upper position H the specimen plate 10 in the cassette 11 transported by the cassette transport mechanism 21 while being gripped with the gripping section 31. The horizontal transport mechanism 23, to be described later, is arranged at the lower position L, the specimen storage device 20 is arranged at the middle position M, and the vertical transport mechanism 22 can also transfer the sample plate 10 with the mechanism 23 and the device 20.

As described above, the vertical transport mechanism 22 merely transports the specimen plate 10 in the up-down direction at the specimen transfer position W and does not transport the specimen plate 10 in the front-back direction or the left-right direction. Therefore, taking out of the specimen plate 10 from the cassette 11, the transfer of the specimen plate 10 with respect to the horizontal transport mechanism 23, to be described later, and the delivery of the specimen plate 10 to the rack 12 transported by the rack transport mechanism 24 are all carried out by the up-down transportation of the specimen plate 10. Thus, the configuration of the vertical transport mechanism 22 can be simplified, and the transportation distance (transportation range) of the specimen plate 10 in a non-protected (non-covered) state can be made as short as possible.

[Configuration of Horizontal Transport Mechanism 23]

As shown in FIG. 1, the horizontal transport mechanism 23 transports the specimen plate 10 in the left-right direction between the specimen transfer position W and a specimen transfer section 4e of the specimen imaging apparatus 4.

The horizontal transport mechanism 23 includes a transportation unit 50 for receiving the specimen plate 10 from the gripping section 31 at the specimen transfer position W and transporting the same in the left direction toward the specimen transfer section (imaging apparatus side transfer position) 4e (see FIG. 1) of the specimen imaging apparatus 4, and receiving the imaged specimen plate 10 from the specimen transfer section 4e and transporting the same in the right direction toward the specimen transfer position W.

Figure 6:
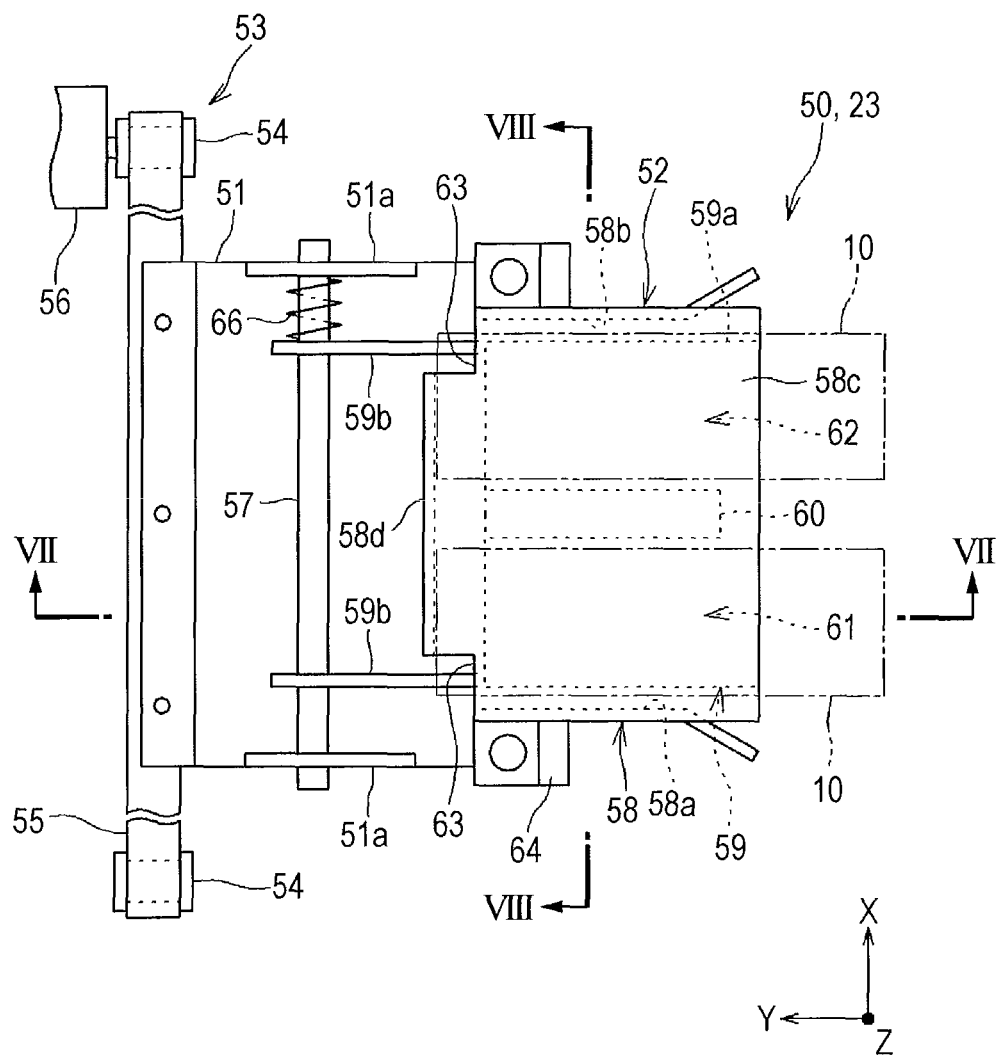
FIG. 6 is a plan explanatory view showing a horizontal transport mechanism.
Figure 7:
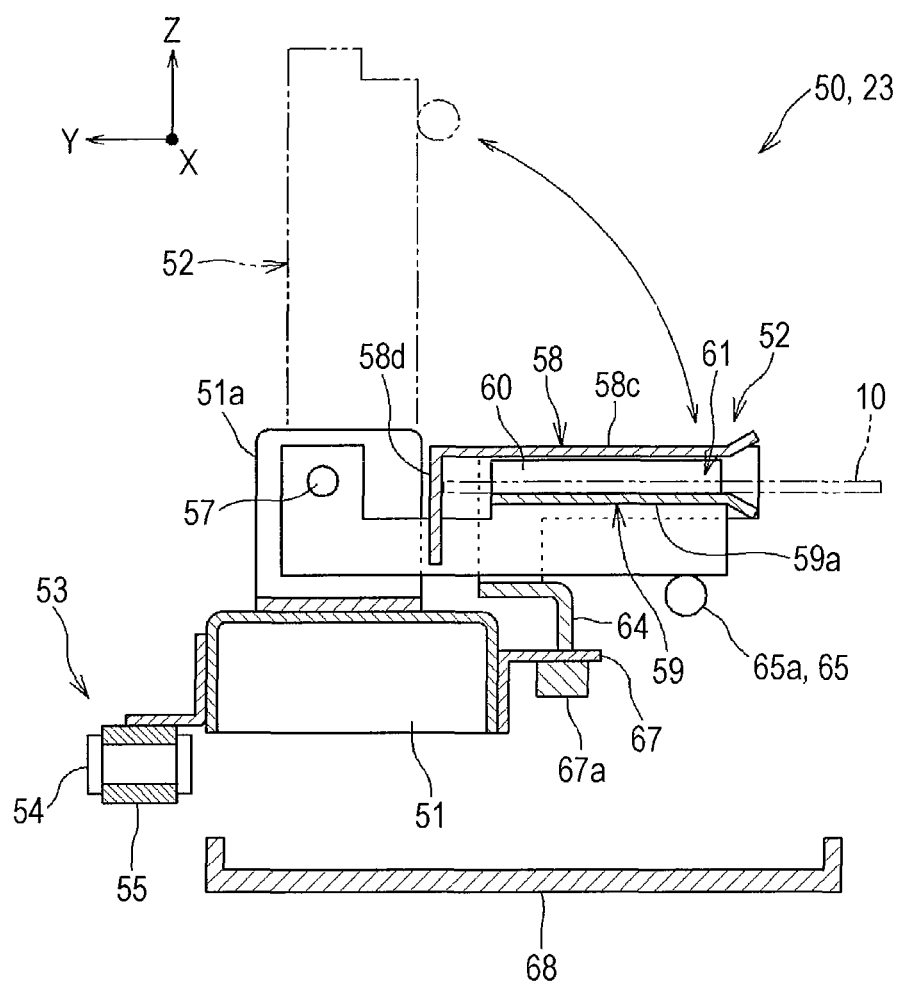
FIG. 7 is a cross-sectional view taken along line VII-VII of FIG. 6.

FIG. 6 is a plan view showing the transportation unit 50 of the horizontal transport mechanism 23, FIG. 7 is a cross-sectional view taken along line VII-VII of FIG. 6, FIGS. 8 A and 8B are cross-sectional views taken along line VIII-VIII of FIG. 6 and are explanatory views showing an operation of a positioning mechanism of the specimen plate 10.

Figure 8A:
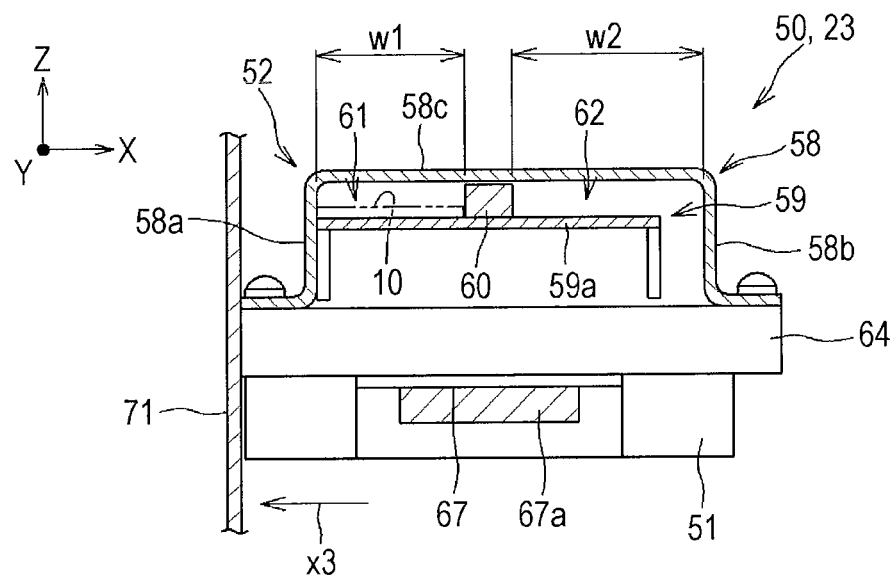
FIGS. 8A and 8B are cross-sectional views taken along line VIII-VIII of FIG. 6.
Figure 8B:
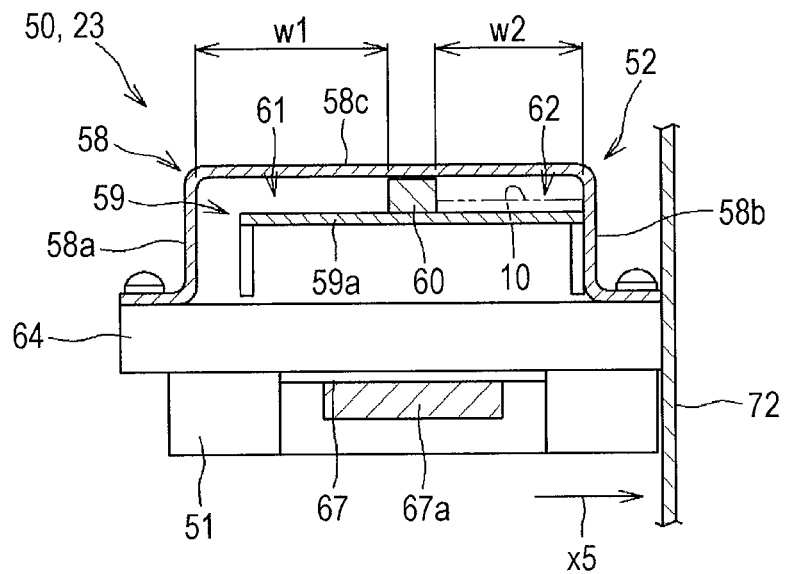

The transportation unit 50 includes a base 51 and the transportation case 52 having a function of a specimen container, and a lateral transport section 53 having a function of a specimen container transport mechanism. The base 51 is supported to be movable in the left-right direction between the specimen transfer position W and the specimen transfer section 4e in the specimen imaging apparatus 4 shown in FIG. 1 by the apparatus frame of the specimen transporter 3. The lateral transport section 53 includes a belt conveyor, and includes a belt 55 wound around a pair of left and right pulleys 54, a drive motor 56 for driving one pulley 54, and the like. A pair of left and right supporting pieces 51a are arranged at the upper part of the base 51, and a supporting shaft 57 having a shaft center in the left-right direction is bridged between the supporting pieces 51a. The transportation case 52 includes a first wall member 58, a second wall member 59, and a partitioning member 60. As shown in FIG. 7 and FIGS. 8A and 8B, the first wall member 58 is bent to a horseshoe-shaped cross-section, and includes left and right side wall portions 58a, 58b, and an upper wall portion 58c. The second wall member 59 includes a lower wall portion 59a opposing at the lower side of the upper wall portion 58c. The partitioning member 60 is arranged at the middle in the left and the right direction of the lower wall portion 59a. A bottom wall portion 58d bent toward the lower side is arranged at the front end portion of the first wall member 58. Therefore, the transportation case 52 is formed with two spaces 61, 62, which are surrounded by the first wall member 58, the second wall member 59, and the partitioning member 60 and opened toward the back side, arranged side by side on the left and the right. Such spaces configure specimen containers where the specimen plate 10 can be contained.

The specimen containers 61, 62 formed in the transportation case 52 include a first container 61 that contains the specimen plate 10 of before being performed with imaging and a second container 62 that contains the specimen plate 10 of after being performed with imaging. The specimen plate 10 is in a state the majority including the sample smearing 10a portion is covered by the transportation case 52 and the portion printed with the sample information 10b is projected out from the transportation case 52 when contained in the first and second containers 61, 62. Furthermore, as shown in FIG. 6, a cutout 63 is formed at a boundary portion of the side wall portion 58a, 58b and the upper wall portion 58c, and the bottom wall portion 58d in the second wall member 59. The cutout 63 serves as an opening for dropping attachments such as immersion oil, and the like, to be described later.

The first wall member 58 and the second wall member 59 of the transportation case 52 are coupled to be relatively movable in the left-right direction. Thus, the dimensional adjustment can be made to a state in which the left-right width w1 of the first container 61 is small and the left-right width w2 of the second container 62 is large, as shown in FIG. 8A, and a state in which the left-right width of the first container 61 is large and the left-right width of the second container 62 is small, as shown in FIG. 8B. In a state in which the left-right widths w1, w2 of the first and second containers 61, 62 are small, the gap between the specimen plate 10 and the left and right side wall portions 58a, 58b and the partitioning member 60 becomes small, so that the rattling in the left-right direction of the specimen plate 10 is suppressed. In a state in which the left-right widths w1, w2 of the first and second containers 61, 62 are wide, the gap between the specimen plate 10 and the left and right side wall portions 58a, 58b and the partitioning member 60 becomes large, and the insertion of the specimen plate 10 with respect to each container 61, 62 is facilitated. A method for adjusting the left-right widths w1, w2 of the first and second containers 61, 62 will be described later.

As shown in FIG. 6 and FIG. 7, a leg member 64 extending in the left-right direction is bridged over the lower end portions of the left and right side wall portions 58a, 58b in the first wall member 58. A coupling arm 59b extending toward the front side is arranged on both left and right sides of the second wall member 59. The distal end of the coupling arm 59b is coupled to the supporting shaft 57 in a freely turning manner. Therefore, the transportation case 52 can be swung up and down (forward and backward) with the supporting shaft 57 as the center, and the swinging enables the posture to be changed to a horizontal posture (reference posture) in which the openings of the first and second containers 61, 62 are directed toward the back side, and a standing posture in which the openings are directed toward the upper side.

The transportation case 52 of the transportation unit 50 has the posture changed by a posture changing mechanism 65. The posture changing mechanism 65 includes an operation bar 65a inserted to the lower side of the transportation case 52 of the transportation unit 50 positioned at the specimen transfer position W, and a drive section 65b (see FIGS. 9A to 9C) for moving the operation bar 65a up and down. The drive section 65b can be configured from a drive motor, a link member, and the like. When the operation bar 65a is moved by the drive section 65b, the transportation case 52 is swung up and down with the supporting shaft 57 as the supporting point to take either the horizontal posture or the standing posture. A biasing member 66 including a torsion coil spring is attached to the supporting shaft 57, and the biasing member 66 biases the transportation case 52 in a direction of swinging to the lower side (direction to become the horizontal posture). Furthermore, as shown in FIG. 7, a supporting section 67 including a magnet (suction member) 67a is arranged at the back part of the base 51, and the leg member 64 coupled to the first wall member 58 is mounted on the supporting section 67 and suctioned to the magnet 67a when the transportation case 52 takes the horizontal posture. The transportation case 52 is thus held in the horizontal posture so as not to lift up by vibration, and the like.

As described with reference to FIG. 3, the specimen plate 10 removed from the cassette 11 by the vertical transport mechanism 22 is positioned at the upper position H of the specimen transfer position W while being gripped by the gripping section 31. As shown in FIG. 4, the specimen plate 10 is transferred to the transportation case 52 of the transportation unit 50 at the lower position L of the specimen transfer position W. In this case, the transportation case 52 is caused to be in the standing posture by the posture changing mechanism 65, and the specimen plate 10 is inserted to the first container 61 of the transportation case 52 by lowering the gripping section 31.

FIGS. 9A to 9C and FIGS. 10A and 10B are schematic plan views describing the operation of the horizontal transport mechanism 23.

Figure 9A:
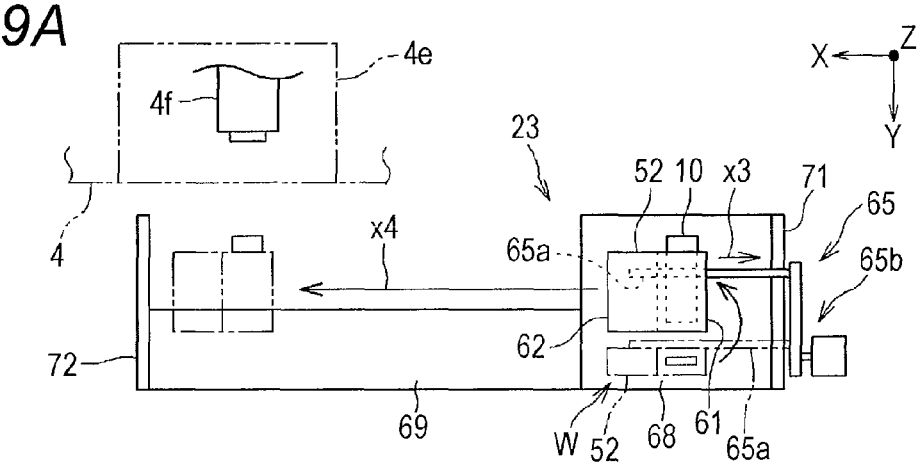
FIGS. 9A to 9C are plan explanatory views showing an operation of the horizontal transport mechanism.
Figure 9B:
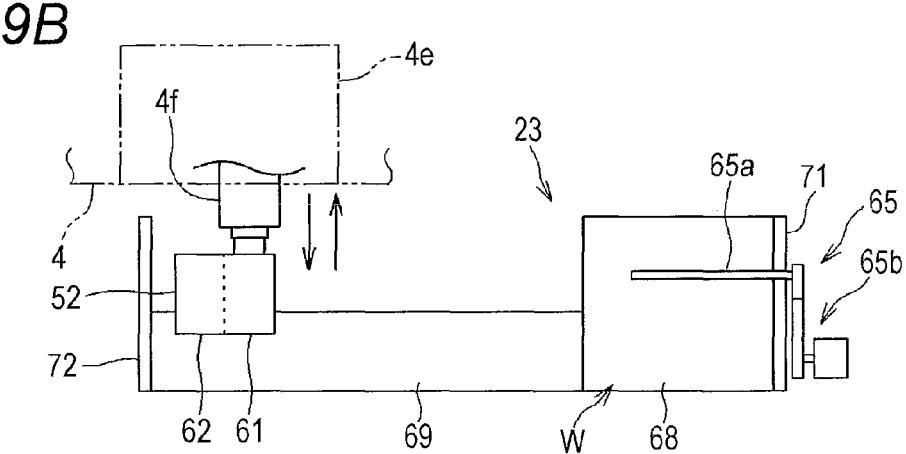
Figure 9C:
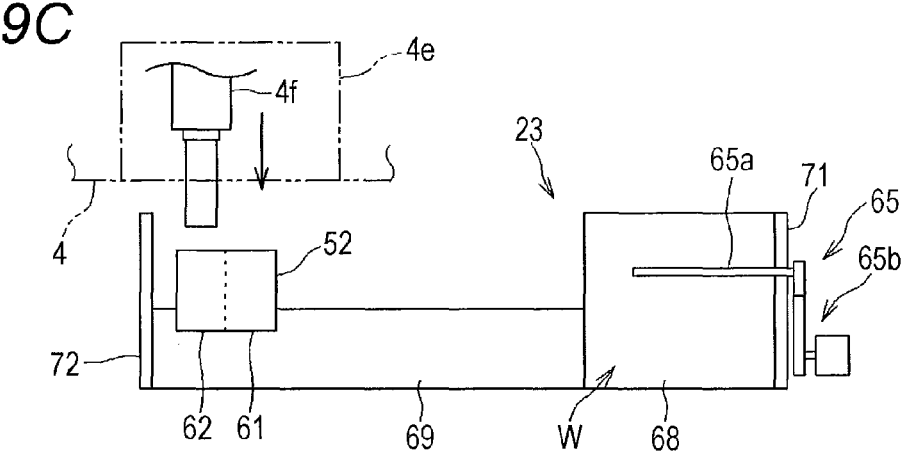
Figure 10A:
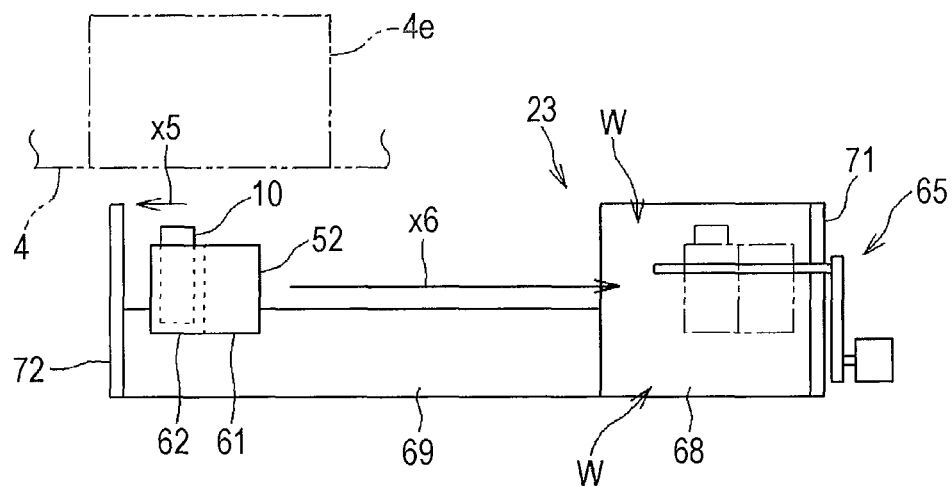
FIGS. 10A and 10B are plan explanatory views showing the operation of the horizontal transport mechanism.
Figure 10B:
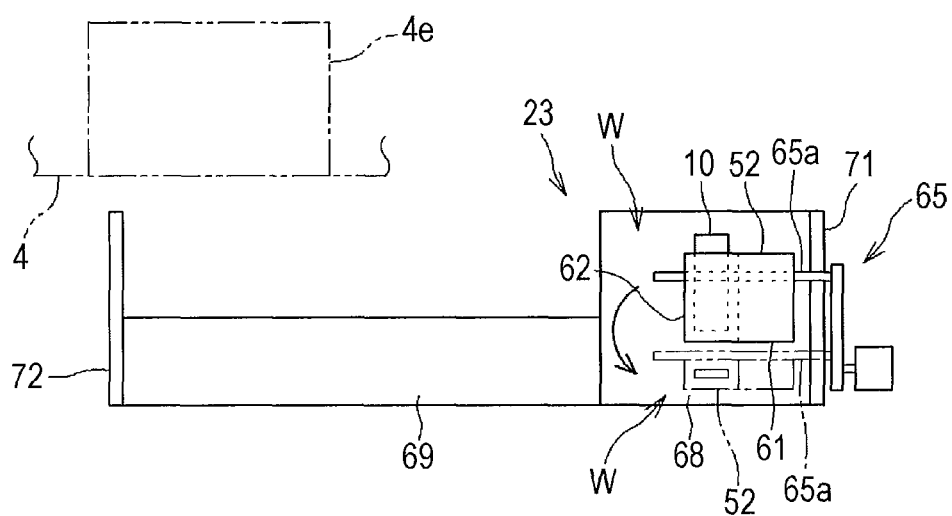
Figure 11:
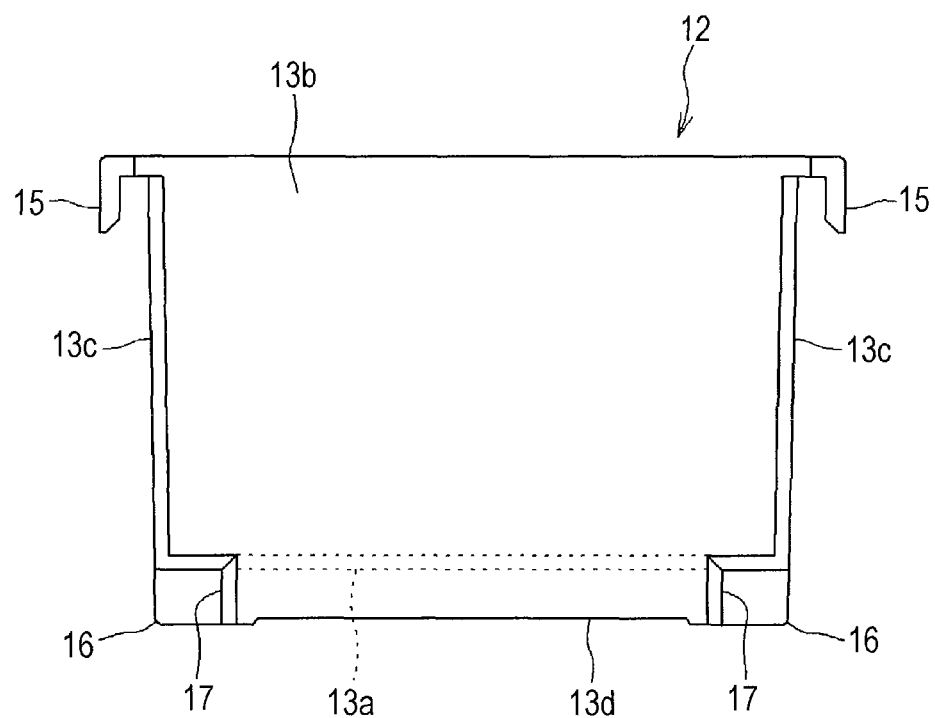
FIG. 11 is a side view of a rack.

As shown in FIGS. 9A to 9C, the specimen plate 10 is inserted to the transportation case 52 of the transportation unit 50 at the specimen transfer position W, and when the posture of the transportation case 52 is changed to the horizontal posture by the posture changing mechanism 65, the lateral transport section 53 (see FIG. 6) is activated to transport the transportation case 52 in the left direction (arrow x4). The transportation case 52 is thereby positioned at the specimen transfer section 4e of the specimen imaging apparatus 4 (see FIG. 9A).

The specimen imaging apparatus 4 includes a transporting section 4f for transporting the specimen plate 10, and the transporting section 4f takes out the specimen plate 10 from the transportation case 52 transported to the specimen transfer section 4e (see FIG. 9B). The specimen plate 10 that is taken out is transported to the imaging section 4a (see FIG. 1) by the transporting section 4f, and the image of the sample is imaged by the imaging section 4a and provided for analysis. The specimen plate 10 performed with imaging (tested) is returned to the specimen transfer section 4e by the transporting section 4f, and returned to the transportation case 52 in standby.

In this case, the specimen plate 10 performed with imaging is inserted to the second container 62 of the transportation case 52 (see FIG. 9C). The transportation case 52 is then transported in the right direction (arrow x6) (see FIG. 10A), and again positioned at the specimen transfer position W. Thereafter, the posture of the transportation case 52 of the transportation unit 50 is changed from the horizontal posture to the standing posture by the posture changing mechanism 65 (see FIG. 9B).

In the operation of the horizontal transport mechanism 23 described above, if the specimen plate 10 to perform the analysis next is supplied to the vertical transport mechanism 22 while analysis is being performed on the specimen plate 10 transported to the specimen imaging apparatus 4, the transportation case 52 is transported from the specimen transfer section 4e to the specimen transfer position W, and the specimen plate 10 to perform the analysis next is contained in the first container 61 of the transportation case 52. Then, the transportation case 52 is positioned at the specimen transfer section 4e of the specimen imaging apparatus 4 by the operation of the lateral transport section 53, and the transporting section 4f takes out the specimen plate 10 to perform the analysis next from the first container 61. The specimen plate 10, which is transported the previous time and which imaging by the specimen imaging apparatus 4 is completed, is then contained in the second container 62 of the transportation case 52. Thus, the operation of taking out the specimen plate 10 to perform the imaging next from the transportation case 52 and the operation of returning the specimen plate 10 performed with imaging to the transportation case 52 can be simultaneously carried out in the specimen transfer section 4e by operating the horizontal transport mechanism 23. The specimen plate 10 thus can be efficiently transported, and the processing ability of the specimen transporter 3 and the specimen testing system 1 can be enhanced.

As described above, the horizontal transport mechanism 23 of the specimen transporter 3 transports the specimen plate 10 taken out from the cassette 11 to the specimen imaging apparatus 4 while being contained in the transportation case 52. Thus, the specimen plate 10 taken out from the cassette 11 is thus covered by the transportation case 52, whereby attachment of dust and the like during the transportation can be prevented. The transportation case 52 of the horizontal transport mechanism 23 separately includes the first container 61 that contains the specimen plate 10 of before being performed with imaging and the second container 62 that contains the specimen plate 10 of after being performed with imaging. Thus, the liquid such as the immersion oil that attached to the specimen plate 10 during the imaging may attach to the second container 62 but will not attach to the first container 61. Thus, the liquid can be prevented from attaching to the specimen plate 10 of before the imaging.

Since an opening (cutout 63, see FIG. 6) is formed at the bottom wall portion 58d of the transportation case 52, the liquid attached to the specimen plate 10 drops to the lower side through the opening and discharged to the outside of the transportation case 52, when the specimen plate 10 performed with imaging is transported to the specimen transfer position W and the transportation case 52 is made to a standing state. As shown in FIG. 7, FIG. 9, and FIG. 10, a liquid receiving tray 68 is arranged at the lower part of the specimen transfer position W, and the attachment of the liquid to other components in the specimen transporter 3, and the like can be prevented by receiving the liquid dropped from the transportation case 52. The liquid receiving tray 68 is attachable/detachable from the apparatus frame of the specimen transporter 3, so that the liquid accumulated on the liquid receiving tray 68 can be easily discarded and the liquid receiving tray 68 can be easily washed by detaching the liquid receiving tray 68. As shown in FIG. 9 and FIG. 10, a liquid receiving plate 69 is arranged on the lower side of the transportation path of the transportation case 52, so that the liquid dropped from the moving transportation case 52 can be received by the liquid receiving plate 69.

The transportation case 52 can contain two specimen plates 10 in a state arranged side by side on the left and the right, and thus the structure can be miniaturized as much as possible. When the transportation case 52 is in the horizontal posture, the height of the specimen plate 10 contained in each container 61, 62 may be made the same, and the transfer height of the specimen plate 10 of before being performed with imaging and after being performed with imaging by the transporting section 4f of the specimen imaging apparatus 4 can be made constant. When the transportation case 52 is in the standing posture, the front-back position of the specimen plate 10 contained in each container 61, 62 may be made the same, and hence the front-back positions of specimen transfer by the gripping section 31 of the vertical transport mechanism 22 can be made constant.

As shown in FIG. 4, when the specimen plate 10 is inserted to the first container 61 of the transportation case 52 by the vertical transport mechanism 22, the left-right width of the first plate container 61 is in a wide state (see FIG. 8B). Thus, the specimen plate 10 can be inserted into the first container 61 with a margin without colliding. However, if the transportation case 52 is transported up to the specimen imaging apparatus 4 in this state, the specimen plate 10 becomes shaky in the first container 61 thus possibly affecting the subsequent transfer of the specimen plate 10. Therefore, in the present embodiment, the transportation case 52 is once moved in the right direction (arrow x3) to make contact with the wall 71 of the apparatus frame before transporting the specimen plate 10 to the specimen imaging apparatus 4, as shown in FIG. 9A. More specifically, as shown in FIG. 8A, the first wall member 58 is moved toward the right side in the figure vis-a-vis to the second wall member 59 by bringing the leg member 64 into contact with the wall 71. The left-right width w1 of the first container 61 thus becomes small, and the rattling of the specimen plate 10 can be eliminated. In this case, the left-right width w2 of the second container 62 becomes relatively large.

The specimen plate 10 performed with imaging is inserted to the second container 62 in the transportation unit 50 by the transporting section 4f in the specimen transfer section 4e of the specimen imaging apparatus 4. In this case, the left-right width w2 of the second container 2 is large, and thus the specimen plate 10 performed with imaging can be inserted to the second container 62 with a margin without colliding. However, if the specimen plate 10 performed with imaging 10 is transported to the specimen transfer position W as it is, the specimen plate 10 may possibly become shaky. Therefore, in the present embodiment, the transportation case 52 is once moved in the left direction (arrow x5) shown in FIG. 10A to make contact with the wall 72 of the apparatus frame before transporting the specimen plate 10 to the specimen transfer position W. More specifically, as shown in FIG. 8B, the first wall member 58 is moved toward the left side in the figure vis-a-vis to the second wall member 59 by bringing the leg member 64 into contact with the wall 72. The left-right width w2 of the second container 62 thus becomes small, and the rattling of the specimen plate 10 can be eliminated.

[Configuration of Specimen Storage Device 20]

The specimen storage device 20 (rack transport mechanism 24, accumulating section 75) is provided to store in the predetermined rack 12, the specimen plate 10 performed with imaging transported to the specimen transfer position W by the horizontal transport mechanism 23 as described above. As shown in FIG. 11 to FIG. 14, the rack 12 has a bottom wall 13a of a rectangular shape in plan view and four side walls 13b, 13c raised toward the upper side from each side of the bottom wall 13a, and has a shape in which the upper side is opened. A total of 12 specimen plates 10 can be stored inside the rack 12. Specifically, the rack 12 can store a plurality of specimen plates 10 so as to be lined in the longitudinal direction of the bottom wall 13a in a substantially perpendicularly standing posture.

A recessed groove (supporting section) 14 extending in the up-down direction is formed in plurals on the front and back on the inner side of the left and right side walls 13b of the rack 12. The specimen plate 10 is supported in the standing posture, and a plurality of specimen plates 10 are stored with a spacing without contacting each other by fitting both side portions of the specimen plate 10 to the recessed groove 14. The recessed groove 14 is formed such that the width becomes wider toward the upper side. Thus, when fitting the specimen plate 10 to the recessed groove 14, the specimen plate 10 is less likely to hit the projecting portion between the recessed grooves 14, and the rattling can be suppressed by inserting the specimen plate 10 to the lower side of the recessed groove 14.

Furthermore, the liquid such as the immersion oil, and the like that attached in imaging flows toward the lower side and is accumulated at the bottom wall 13a of the rack 12 since the specimen plate 10 is stored in a standing state. Thus, the liquid does not spill out to the outside or get the moving region of the rack 12, and the like dirty. A recess 13d is formed at the lower end side of the left and right side walls 13b, and the contacting area with respect to the bottom plate 80 of the accumulating section 75, to be described later, is reduced by the recess 13d. The resistance of when the rack 12 slidably moves on the bottom plate 80 is thus reduced.

A hook portion 15 bent toward the lower side is formed at the upper end portion of the front and back side walls 13c of the rack 12. The rack 12 is formed to be plane symmetric with respect to a perpendicular plane passing through the front-back center line 01 and plane symmetric with respect to a perpendicular plane passing through the left-right center line 02 in the plan view of FIG. 12. In other words, the rack 12 is formed to be rotation symmetric (dyad symmetric) with respect to the central line C of the rack 12 in plan view. Therefore, when setting the rack 12 with respect to the accumulating section 75 of the specimen transporter 3, the rack can be set without taking the direction of the front-back direction into consideration.

Figure 13:
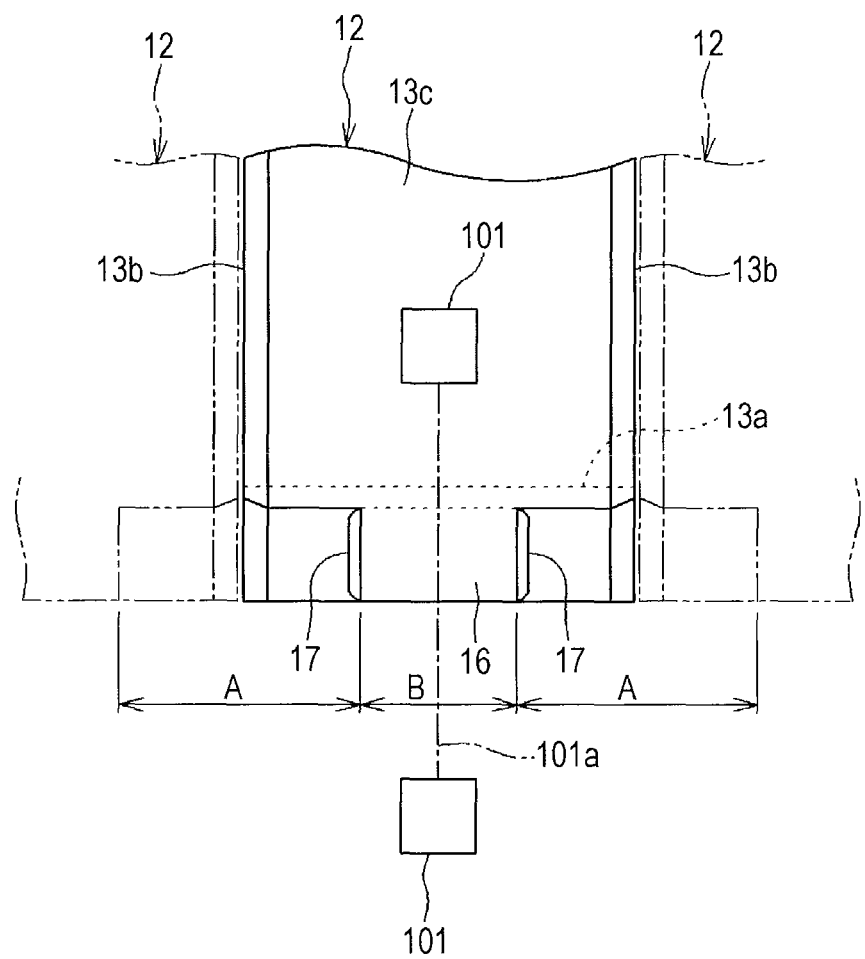
FIG. 13 is a front view showing a lower part of the rack.
Figure 14:
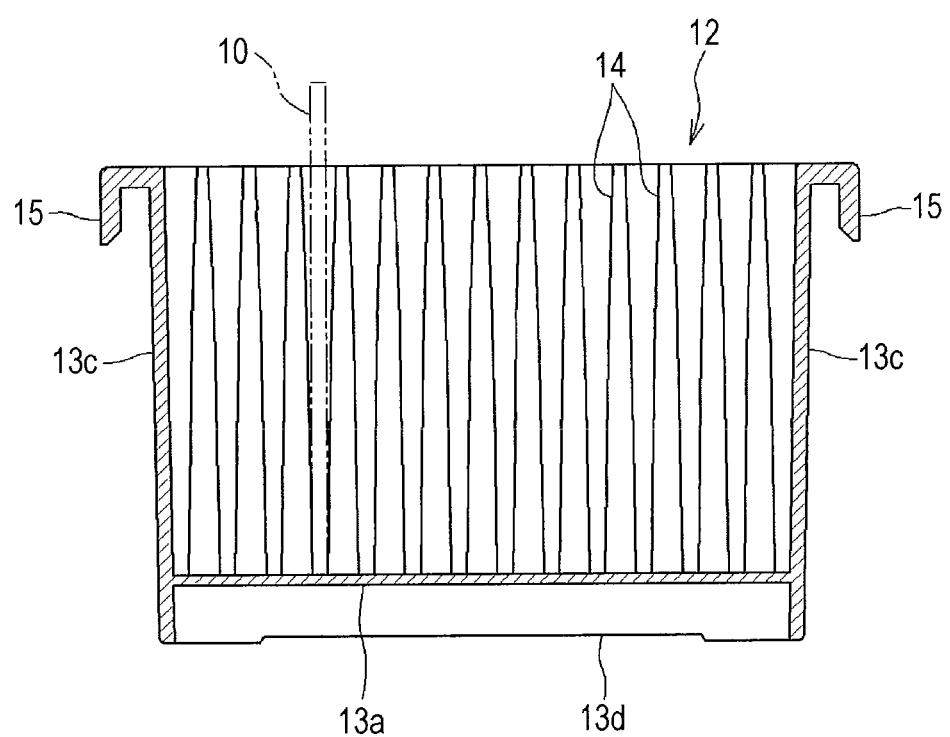
FIG. 14 is a cross-sectional view taken along line XIV-XIV of FIG. 12.

As shown in FIG. 13, a recess 17 is formed on both left and right sides of the lower end portion in the front and back side walls 13c of the rack 12. A portion between the recesses 17 on both left and right sides is a detected portion 16 to be detected by a sensor (detector) for detecting whether or not the rack 12 exists at a predetermined position (take-out collecting position R) in the accumulating section 75, to be described later.

As shown in FIG. 1, the specimen storage device 20 includes the accumulating section 75 capable of accumulating a plurality of racks 12 so as to be lined in the left-right direction, and the rack transport mechanism 24 for transporting the rack 12 in the horizontal direction at the inside and the outside of the accumulating section 75. The rack transport mechanism 24 includes a lateral transport section 76 (see FIG. 15) for transporting the rack 12 in the left-right direction, and a longitudinal transport section 77 for transporting the rack 12 in the front-back direction from the predetermined position R in the accumulating section 75. The accumulating section 75 is arranged on the front side of the specimen transfer position W, and the longitudinal transport section 77 is arranged to transverse the specimen transfer position W in the front-back direction.

Figure 15:
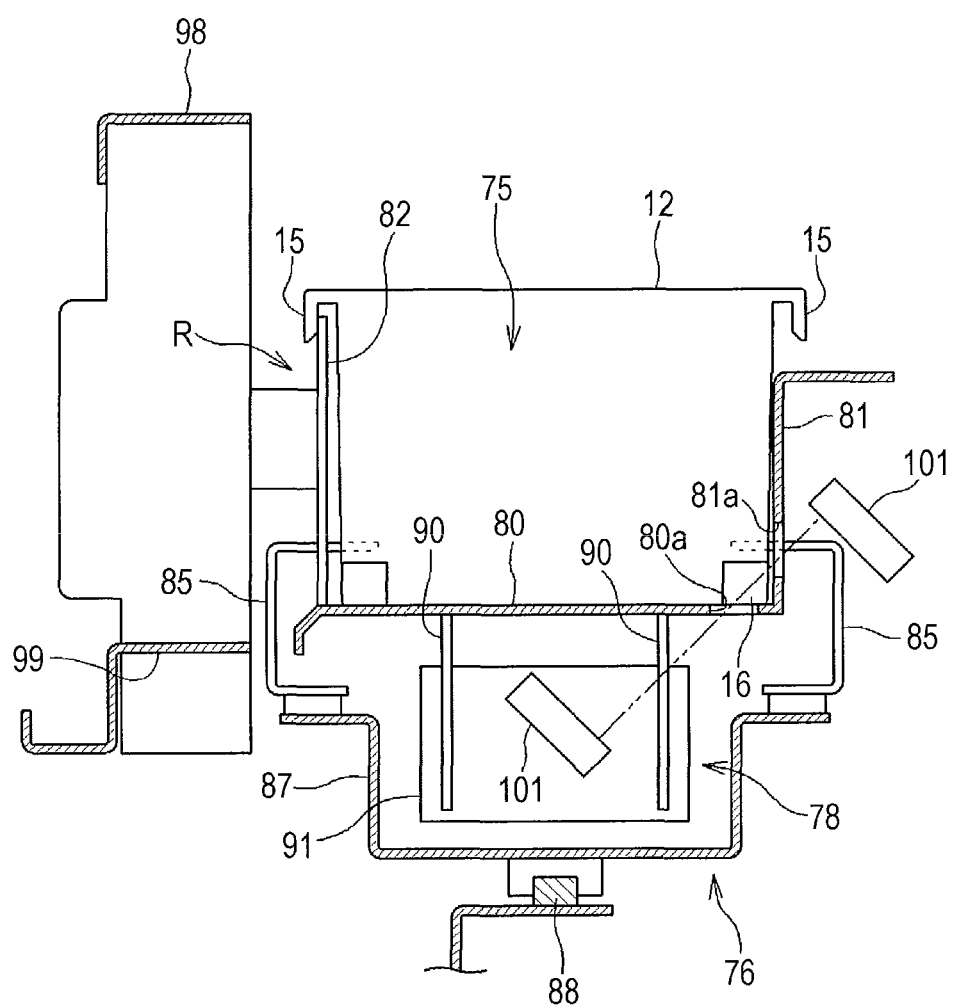
FIG. 15 is a cross-sectional explanatory view of a rack transport mechanism seen from the side.
Figure 16:
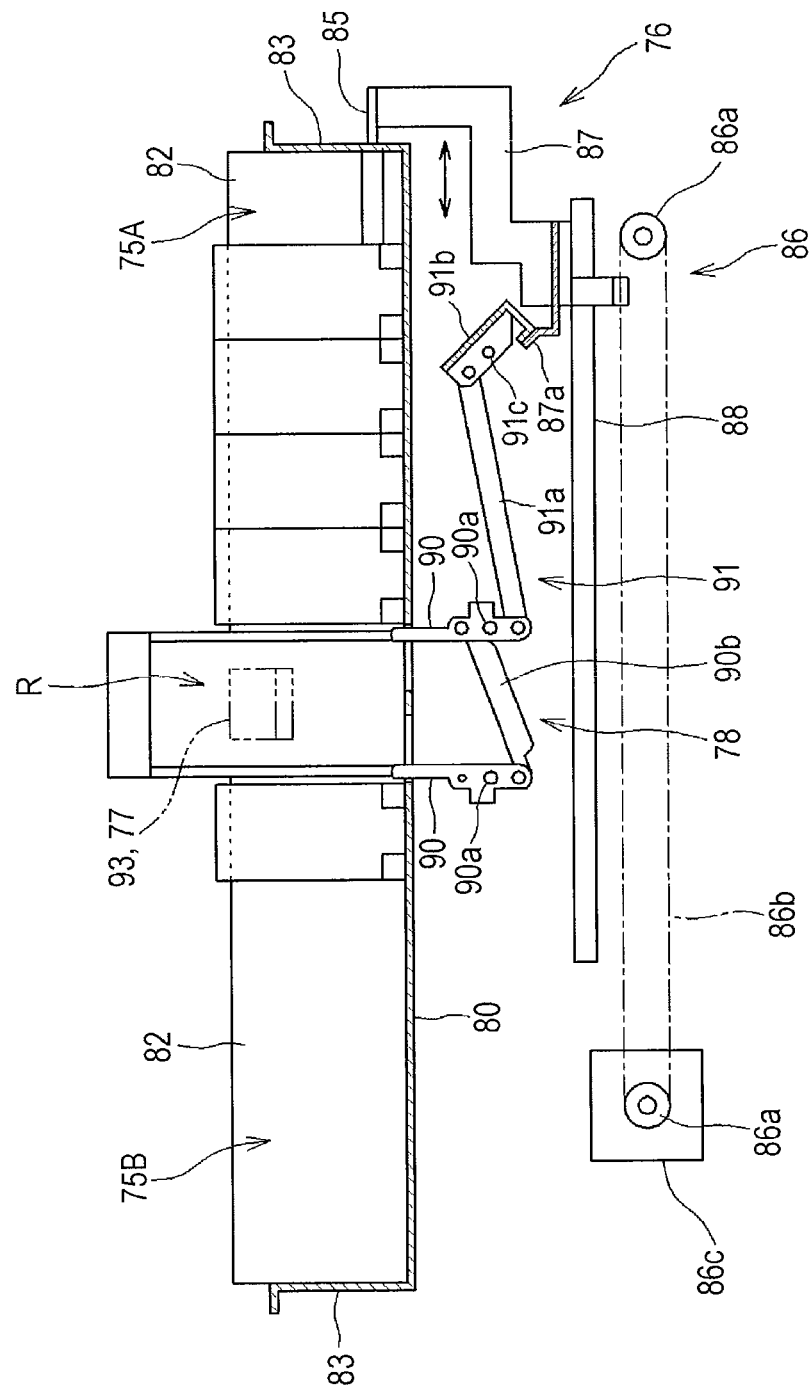
FIG. 16 is a cross-sectional explanatory view of the rack transport mechanism seen from the front.
Figure 17:
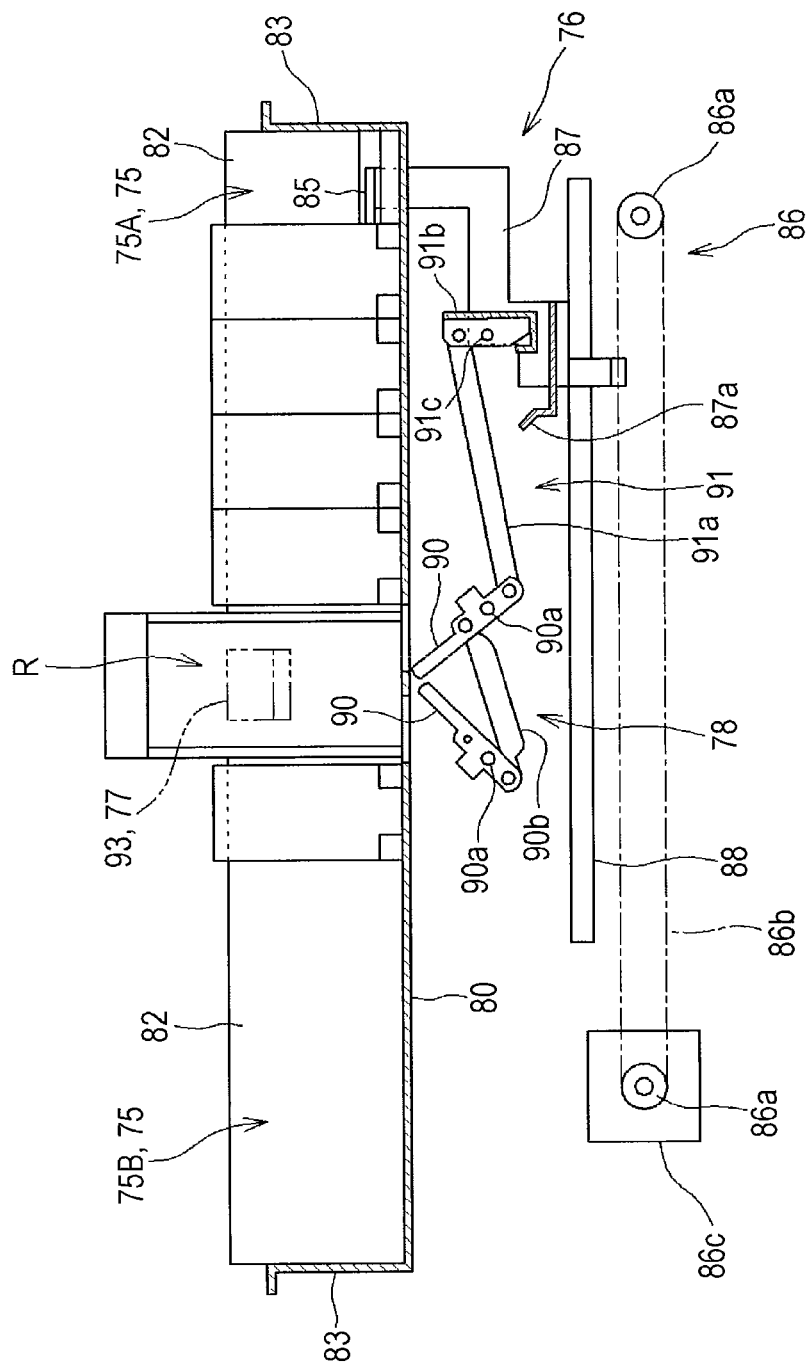
FIG. 17 is a cross-sectional explanatory view of the rack transport mechanism seen from the front.

FIG. 15 is a cross-sectional explanatory view of the rack transport mechanism 24 seen from the side, and FIG. 16 and FIG. 17 are cross-sectional explanatory views of the rack transport mechanism 24 seen from the front.

The accumulating section 75 includes the bottom plate 80 formed to a rectangular shape that is long in the left-right direction in plan view, and front and back plates 81, 82 and left and right plates 83 raised from the four sides of the bottom plate. A plurality of racks 12 is mounted on the bottom plate 80 to accumulate the same. The accumulating section 75 of the present embodiment has the take-out collecting position R of the rack 12 set at a central part in the left-right direction. At the take-out collecting position R, the rack 12 is taken out from the accumulating section 75, and the specimen plate 10 is stored with respect to the rack 12. The rack 12 in which the storing of the specimen plate 10 is completed is again returned to the take out collecting position R.

A pre-stage accumulating section (second accumulating section) 75A for accumulating an empty rack 12, in which the specimen plate 10 is not stored, is arranged on the right side of the take-out collecting position R in the accumulating section 75, and a post-stage accumulating section (first accumulating section) 75B for accumulating the rack 12, in which the used specimen plate 10 is stored, is arranged on the left side of the take-out collecting position R.

As shown in FIG. 16, the back plate 82 of the accumulating section 75 is formed only at the portions of the pre-stage accumulating section 75A and the post-stage accumulating section 75B, and is not arranged at the take-out collecting position R. Thus, the rack 12 arranged at the take-out collecting position R can be pulled out toward the back side. Furthermore, as shown in FIG. 15, the hook portion 15 on the back side of the rack 12 stored in the pre-stage accumulating section 75A and the post-stage accumulating section 75B is engaged with the upper end portion of the back plate 82. Thus, the overturning in the left-right direction of the rack 12 in the accumulating sections 75A, 75B is prevented. Therefore, the hook portion 15 formed on the rack 12 and the back plate 82 of the accumulating sections 75A, 75B function as an overturning preventing means for preventing the overturning of the rack 12.

The lateral transport section 76 is configured to transport the rack 12 in the accumulating section 75 to the right and the left. In other words, the lateral transport section 76 transports the rack 12 from the pre-stage accumulating section 75A to the post-stage accumulating section 75B through the take-out collecting position R. More specifically, the lateral transport section 76 includes a pusher member 85 that engages a rack 12 at the right most side (back part side in the transporting direction) among the plurality of racks 12 contained in the pre-stage accumulating section 75A, and a drive section 86 for moving the pusher member 85 in the left-right direction.

As shown in FIG. 15, a pair of front and back pusher members 85 are arranged, and can engage the front end portion and the back end portion of the rack 12, respectively. The pair of front and back pusher members 85 are coupled by a coupling member 87 at the lower side of the accumulating section 75, and the movement in the left-right direction of the coupling member 87 is guided by a guide rail 88 extending in the left-right direction.

As shown in FIG. 16 and FIG. 17, the drive section 86 is configured by a belt conveyor. Specifically, the drive section 86 includes a pair of left and right pulleys 86a, a belt 86b wound around the pulleys 86a, and a drive motor 86c for driving one pulley 86a. The coupling member 87 is coupled to the belt 86b.

When the belt 86b is sent by the operation of the drive motor 86c, the pusher member 85 moves in the left-right direction through the coupling member 87. All the racks 12 on the accumulating section 75 can be moved in the left direction by engaging the pusher member 85 with the rack 12 on the right most side and moving the same in the left direction. As shown in FIG. 16, the pusher member 85 has the right end portion of the pre-stage accumulating section 75A as an initial position, and can move the rack 12 by moving in the left direction from the initial position.

The rack 12 transported to the take-out collecting position R by the lateral transport section 76 is taken out from the accumulating section 75 by the longitudinal transport section 77, to be described later, and a stopper mechanism (transportation inhibiting mechanism) 78 for inhibiting the transportation so that the rack 12 existing other than at the take-out collecting position R does not enter the take-out collecting position R by mistake is arranged.

As shown in FIG. 16 and FIG. 17, at both left and right sides of the take-out collecting position R, the stopper mechanism 78 includes a transportation inhibiting member 90 that projects out on the bottom plate 80 of the accumulating section 75 to act on the rack 12, and a switching section 91 for switching between an acting state in which the transportation inhibiting member 90 projects out from the bottom plate 80 and a non-acting state in which the transportation inhibiting member 90 is evacuated to the lower side of the bottom plate 80. As shown in FIG. 15, two transportation inhibiting members 90 are arranged in a front and back manner at each of the left and the right of the take-out collecting position R.

Each transportation inhibiting member 90 is turnably attached about a supporting shaft 90a in the front-back direction at the lower side of the bottom plate 80. The transportation inhibiting members 90 facing each other in the left-right direction are coupled by a link member 90b to swing in cooperation. Specifically, the left and right transportation inhibiting members 90 are evacuated from the bottom plate 80 by being swung in a direction of approaching each other, and are projected out on the bottom plate 80 by being swung in a direction of separating from each other.

The switching section 91 includes a drive link 91a having one end coupled to a lower end portion of the transportation inhibiting member 90 on the right side, and an interlocking link 91b having one end coupled to the other end of the drive link 91a. The interlocking link 91b has a central part turnably attached about a supporting shaft 91c in the front-back direction, and the drive link 91a is coupled to the upper end portion. An engagement member 87a that moves with the coupling member 87 of the lateral transport section 76 is engaged with the lower end portion of the interlocking link 91b. Furthermore, the interlocking link 91b is biased in a clockwise direction by a biasing member (not shown).

Therefore, the stopper mechanism 78 operates in cooperation with the operation of the lateral transport section 76. Specifically, as shown in FIG. 16, when the pusher member 85 is at the initial position on the right end, the engagement member 87a engages the interlocking link 91b and the transportation inhibiting member 90 is in the acting state of projecting out from the bottom plate 80. In this state, the racks 12 in the pre-stage accumulating section 75A and the post-stage accumulating section 75B cannot enter the take-out collecting position R. The rack 12 also cannot move to the take-out collecting position R since the pusher member 85 is at the initial position.

As shown in FIG. 17, when the pusher member 85 is moved in the left direction from the initial position to push the rack 12, the engagement member 87a is disengaged from the interlocking link 91b so that the transportation inhibiting member 90 is in the non-acting state through the drive link 91a. Therefore, the rack 12 pushed by the pusher member 85 can be transported in the accumulating section 75 without being inhibited by the transportation inhibiting member 90.

Thus, the stopper mechanism 78 (transportation inhibiting member 90) operates in cooperation with the lateral transport section 76, and is driven by the same drive section as the drive section 86 of the lateral transport section 76. Therefore, the structure can be simplified compared to when driving the relevant components with separate drive sections.

Figure 21:
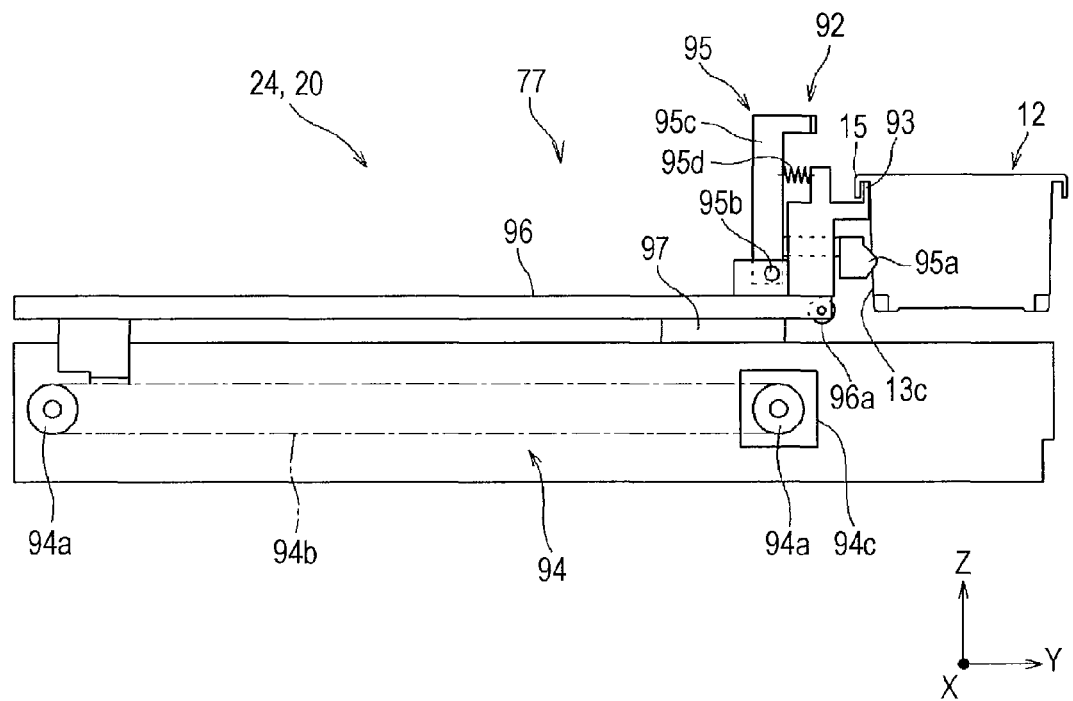
FIG. 21 is a side explanatory view showing a longitudinal transport section (retreated state) of the rack transport mechanism.
Figure 22:
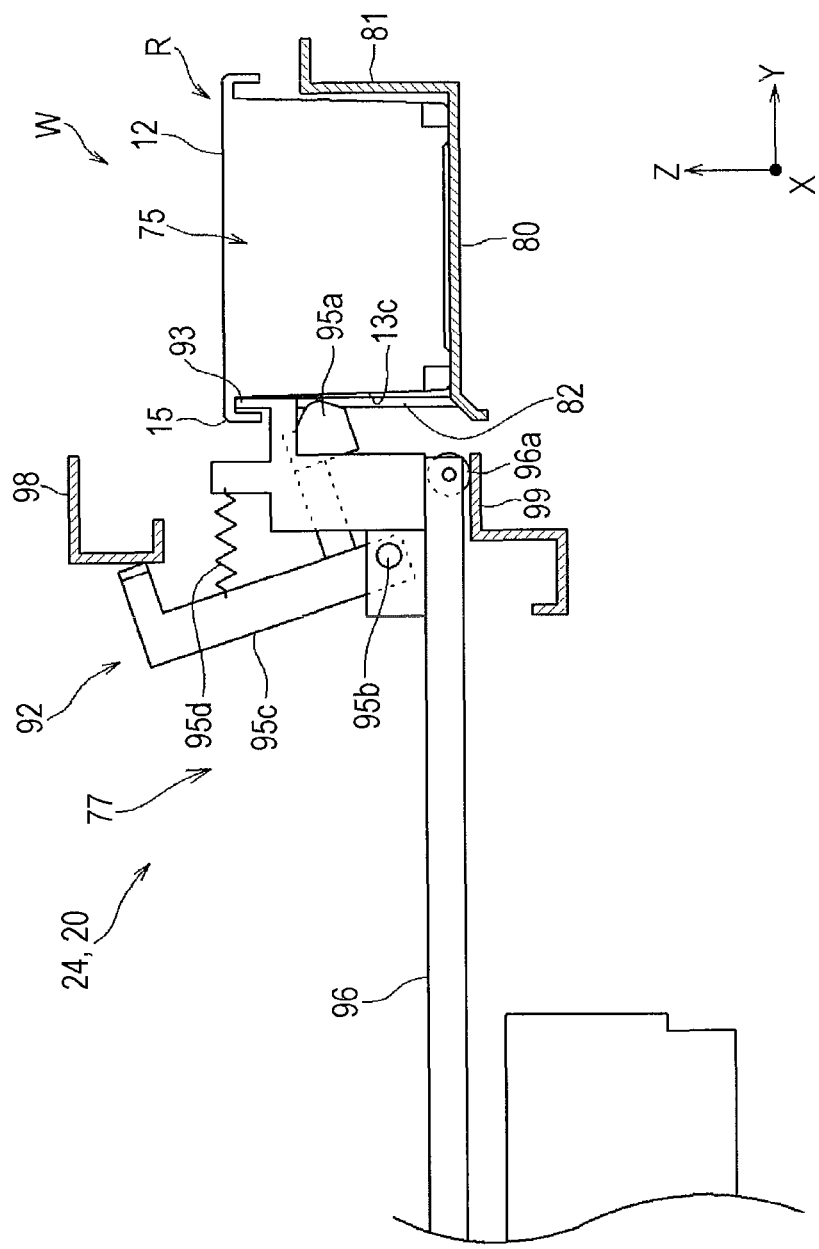
FIG. 22 is a side explanatory view showing the longitudinal transport section (advanced state) of the rack transport mechanism.

FIG. 21 is a side explanatory view showing the longitudinal transport section 77 (retreated state) of the rack transport mechanism 24, and FIG. 22 is a side explanatory view showing the longitudinal transport section 77 (advanced state) of the rack transport mechanism 24.

The longitudinal transport section 77 has a function of taking out the rack 12 at the take-out collecting position R from the accumulating section 75 by moving it backward by the lateral transport section 76, transporting the rack 12 to a storage position of the specimen plate 10 (specimen transfer position W described above), and again returning the rack 12 of after being stored with the specimen plate 10 back to the accumulating section 75.

The longitudinal transport section 77 includes a supporting section 92 for supporting the rack 12, and a drive section 94 for moving the supporting section 92 in the front-back direction. The supporting section 92 includes an engagement nail 93 for engaging the hook portion 15 on the back side of the rack 12, a posture holder 95 for holding the posture of the rack 12 engaged to the engagement nail 93, and a movement member 96 having the engagement nail 93 and the posture holder 95 attached to the front end.

The movement member 96 is a long member formed to be long in the front-back direction, and is supported to be movable in the front-back direction by a guide section 97.

The drive section 94 includes a belt conveyor, and includes a pair of front and back pulleys 94a, a belt 94b wound around the pulleys 94a, and a drive motor 94c for driving one pulley 94a. A back end portion of the movement member 96 is coupled to the belt 94b. Therefore, the engagement nail 93 and the posture holder 95 can be moved in the front-back direction through the movement member 96 by the operation of the drive motor 94c. The position of the engagement nail 93 shown in FIG. 21 is a most retreated initial position.

The engagement nail 93 supports the rack 12 in a lifted state by engaging with the hook portion 15 on the back side of the rack 12. The front portion side of the rack 12 tilts downward if the engagement nail 93 is merely engaged with the hook portion 15, and hence the posture of the rack 12 is held horizontal by bringing the posture holder 95 into contact with the back side wall 13c of the rack 12. The posture holder 95 includes a holder main body 95a that makes contact with the rack 12, and an operation member 95c swingably arranged about a supporting shaft 95b in the left-right direction on the movement member 96. The operation member 95c is biased to swing toward the front side by a biasing member 95d including a tension coil spring bridged between the operation member 95c and the engagement nail 93.

FIG. 22 shows a state in which the engagement nail 93 and the posture holder 95 are advanced toward the front side the most by the longitudinal transport section 77. In this case, the engagement nail 93 is arranged at a position lined in the left-right direction with the upper end portion of the back plate 82 of the accumulating section 75. Therefore, when the rack 12 is transported to the take-out collecting position R by the lateral transport section 76, the hook portion 15 on the back side thereof automatically engages with the engagement nail 93. The operation member 95c of the posture holder 95 makes contact with a contacting portion 98 arranged on the upper back side of the accumulating section 75 so as to be swung toward the back side. Thus, the holder main body 95a of the posture holder 95 is in a state retreated from the back side wall 13c of the rack 12 so as not to inhibit the lateral transportation of the rack 12. A roller 96a is attached to the lower surface of the front end portion of the movement member 96, and the roller 96a is mounted on a supporting board 99 arranged on the lower back side of the accumulating section 75. The front end portion of the movement member 96 is thereby supported, so that the engagement nail 93 is positioned at an appropriate position in the up-down direction.

FIGS. 18A to 18C to FIGS. 20A and 20B are schematic plan views describing the operation of the lateral transport section 76 of the rack transport mechanism 24.

Figure 18A:
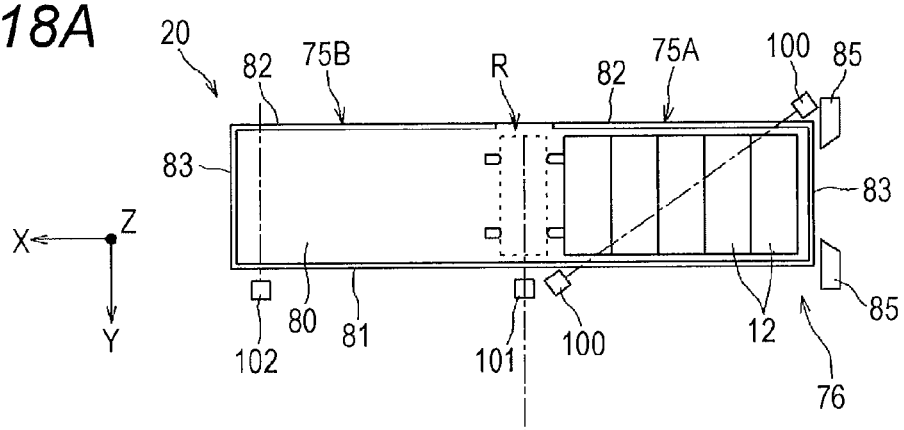
FIGS. 18A to 18C are schematic plan views describing the operation of the lateral transport section of the rack transport mechanism.

FIG. 18A shows a state in which five empty racks 12 are accumulated in the pre-stage accumulating section 75A. Whether or not there is a rack 12 in the pre-stage accumulating section 75A can be detected with a sensor 100. The sensor 100 is configured by a pair of light projecting/receiving units having an optical axis that diagonally passes the pre-stage accumulating section 75A. The pusher member 85 of the lateral transport section 76 is arranged at the initial position on the right end. Furthermore, whether or not there is a rack 12 in the post-stage accumulating section 75B can be detected with a sensor 102. The sensor 102 is configured by a reflective light projecting/receiving unit arranged at the left end of the post-stage accumulating section 75B. When the rack 12 is transported to the left end of the post-stage accumulating section 75B, that is, when the post-stage accumulating section 75B becomes full, the light signal reflected by the rack 12 at the left end is received by the sensor 102 thus detecting that the post-stage accumulating section 75B is full.

Figure 18B:
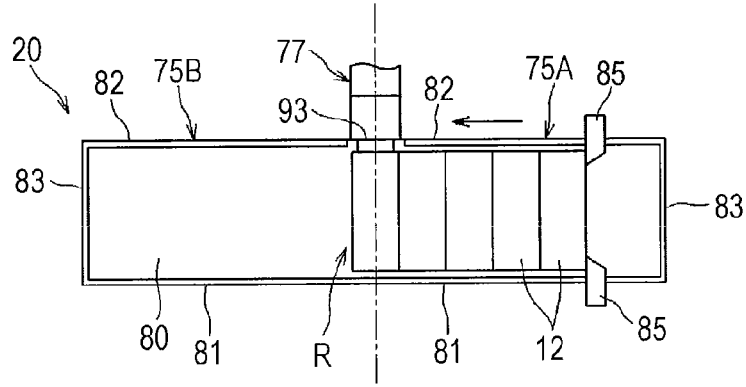

In FIG. 18B, when the pusher member 85 is moved in the left direction, all the racks 12 in the pre-stage accumulating section 75A are pushed in the left direction. The operation of the pusher member 85 is stopped when the rack 12 at the most left side is positioned at the take-out collecting position R. In this case, the hook portion 15 (see FIG. 22) of the rack 12 positioned at the take-out collecting position R engages with the engagement nail 93 of the longitudinal transport section 77 waiting at the relevant position R.

Whether or not the rack 12 is positioned at the take-out collecting position R may be detected with a sensor 101. As shown in FIG. 15, the sensor 101 includes a pair of light projecting/receiving units having an optical axis 101a that passes through holes 81a, 80a formed in the front plate 81 and the bottom plate 80 of the accumulating section 75, respectively. The sensor 101 can detect that the rack 12 is positioned at the take-out collecting position R when the optical axis 101a is shielded by a detected portion 16 formed at the lower end portion of the front side wall 13c of the rack 12. In other words, as shown in FIG. 13, the existence of the rack 12 is not detected if the optical axis 101a of the sensor 101 is in a range A (non-detecting region) of the recesses 17 of the rack 12 lined side by side to the left and right, and the existence of the rack 12 is detected if the optical axis 101a is in a range B (detecting region) of the detected portion 16. Thus, the detecting region B and the non-detecting region A are alternately arranged when the plurality of racks 12 are lined to the left and right, so that each rack 12 can be reliably detected by the sensor 101.

Figure 18C:
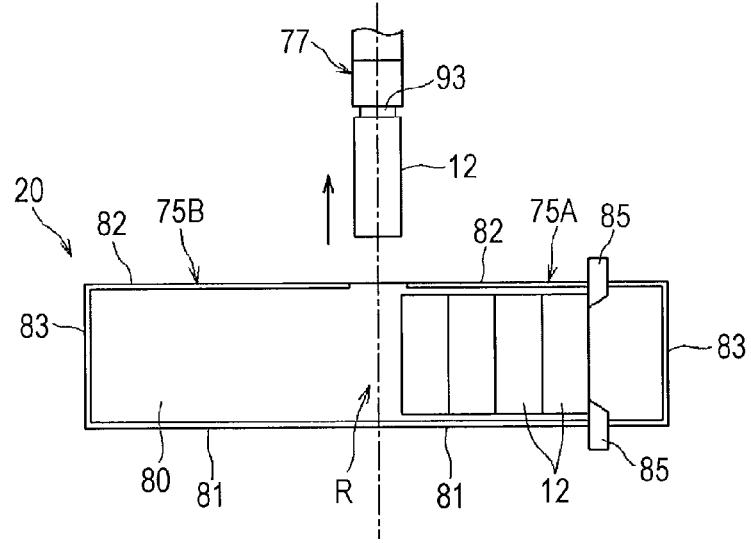

Thereafter, as shown in FIG. 18C, the rack 12 is taken out from the take-out collecting position R when the engagement nail 93 of the longitudinal transport section 77 is moved toward the back side. The specimen plate 10 performed with imaging is sequentially stored in the rack 12 taken out. The details of such operation will be described later.

Figure 19A:
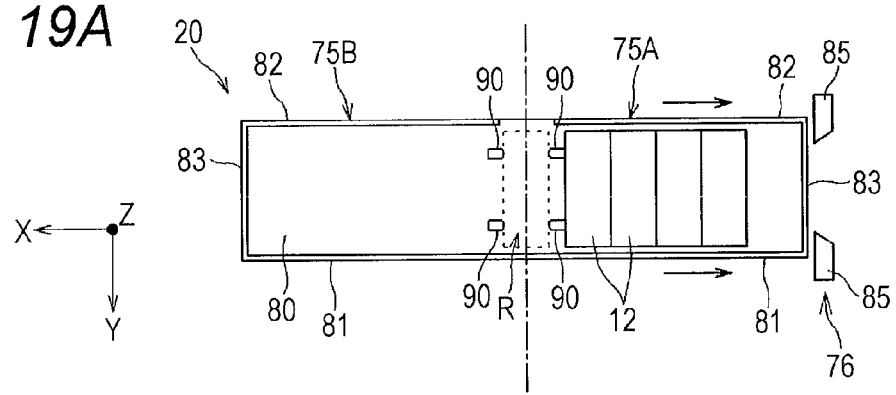
FIGS. 19A to 19C are schematic plan views describing the operation of the lateral transport section of the rack transport mechanism.
Figure 19B:
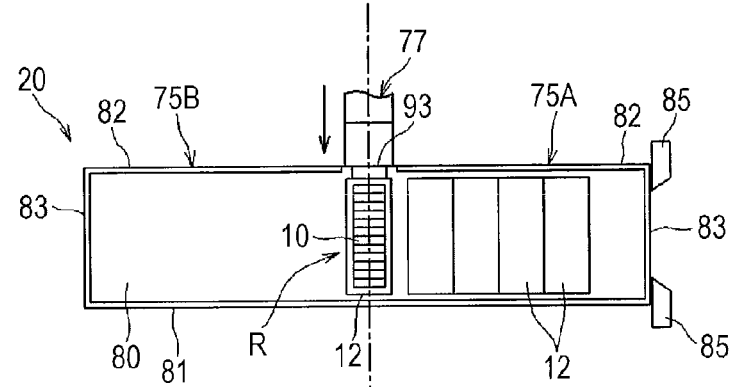

As shown in FIG. 19A, when the pusher member 85 is moved in the right direction and positioned at the initial position, the transportation inhibiting member 90 projects out on the bottom plate 80 of the accumulating section 75. The racks 12 remaining in the pre-stage accumulating section 75A thus can be prevented from entering the take-out collecting position R. As shown in FIG. 19B, when the rack 12 of after storing the specimen plate 10 is advanced forward by the longitudinal transport section 77 and returned to the take-out collecting position R, the pusher member 85 is slightly moved in the left direction and the transportation inhibiting member 90 is evacuated to the lower side of the bottom plate 80. In the present embodiment, the longitudinal transport section 77 does not move the rack 12 to the take-out collecting position R when the transportation inhibiting member 90 is projecting out on the bottom plate 80.

In FIG. 19A, when the transportation inhibiting member 90 is projecting out on the bottom plate 80, the rack 12 of the pre-stage accumulating section 75A is slightly pushed back in the right direction. This is because the movement in the right direction is involved when the transportation inhibiting member 90 on the right side projects out from the bottom plate 80, as shown in FIG. 16 and FIG. 17. Wider space of the take-out collecting position R can be ensured and interference with another rack 12 in the accumulating section 75 can be prevented when the rack 12 of after storing the specimen plate 10 is returned to the take-out collecting position R by pushing back the rack 12 of the pre-stage accumulating section 75A in the right direction.

Figure 19C:
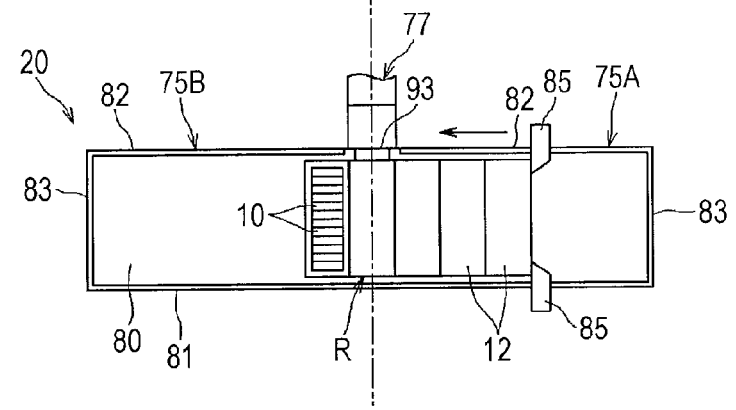
Figure 20A:
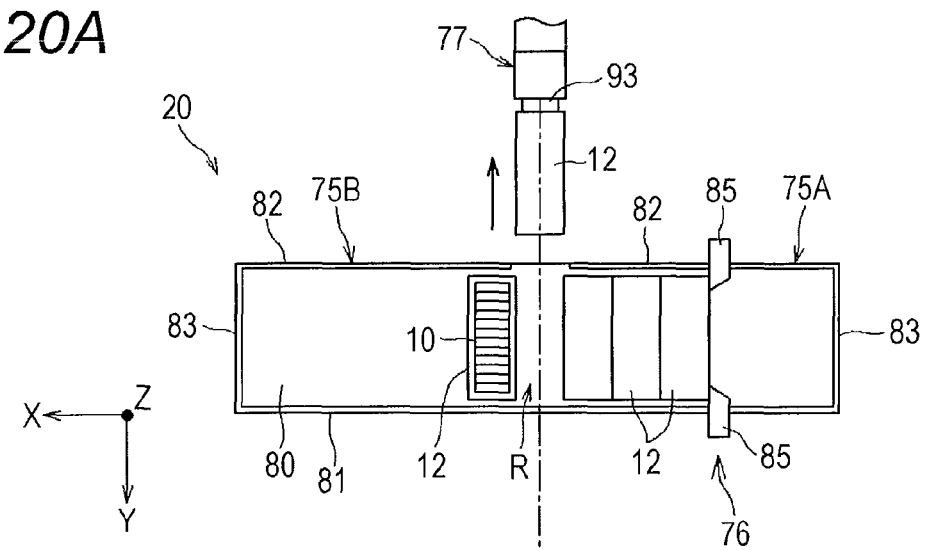
FIGS. 20A and 20B are schematic plan views describing the operation of the lateral transport section of the rack transport mechanism.

Then, as shown in FIG. 19C, the pusher member 85 at the initial position is further moved in the left direction, and the four empty racks 12 in the pre-stage accumulating section 75A and the rack 12 storing the specimen plate 10 at the take-out collecting position R are all moved in the left direction. When the empty rack 12 is positioned at the take-out collecting position R, the pusher member 85 stops the operation and the rack 12 is taken out toward the back side by the longitudinal transport section 77, as shown in FIG. 20A.

Figure 20B:
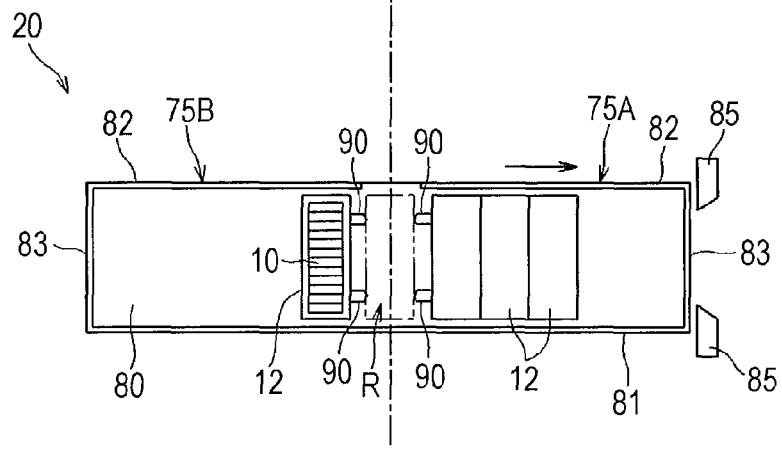

Thereafter, when the pusher member 85 is returned to the initial position, the transportation inhibiting member 90 again projects out on the bottom plate 80, as shown in FIG. 20B. In this case, the rack 12 storing the specimen plate 10 is slightly pushed in the left direction by the transportation inhibiting member 90, and the empty rack 12 is pushed back slightly in the right direction by the transportation inhibiting member 90, so that a wide space of the take-out collecting position R can be ensured.

The operation of storing the specimen plate 10 performed with imaging in the rack 12 will now be described.

Figure 23A:
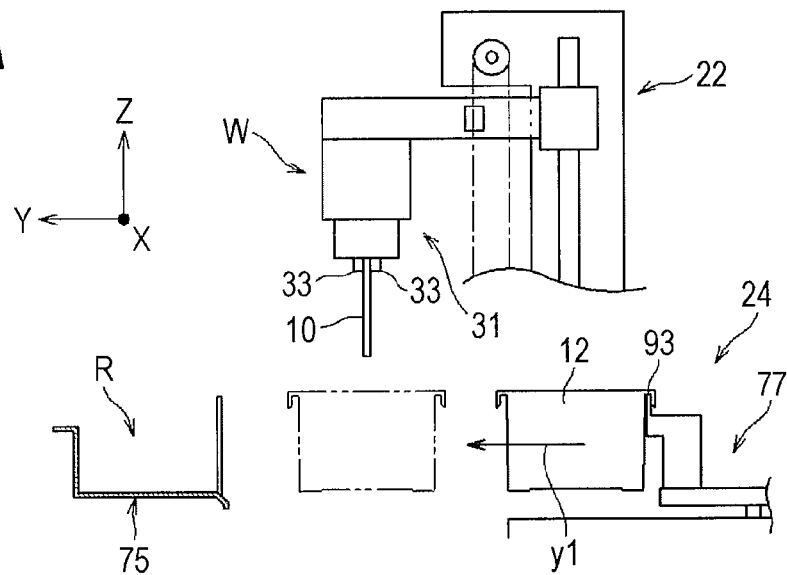
FIGS. 23A to 23C are schematic side views describing the operation of the longitudinal transport section.
Figure 23B:
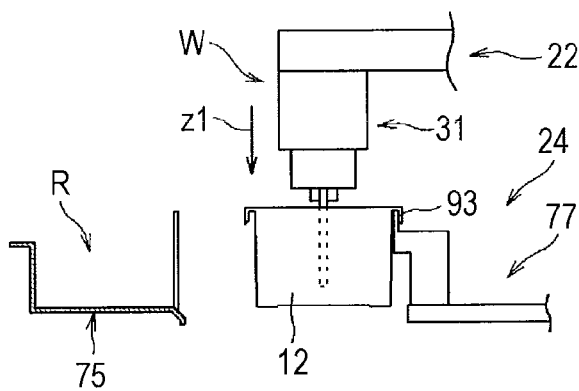
Figure 23C:
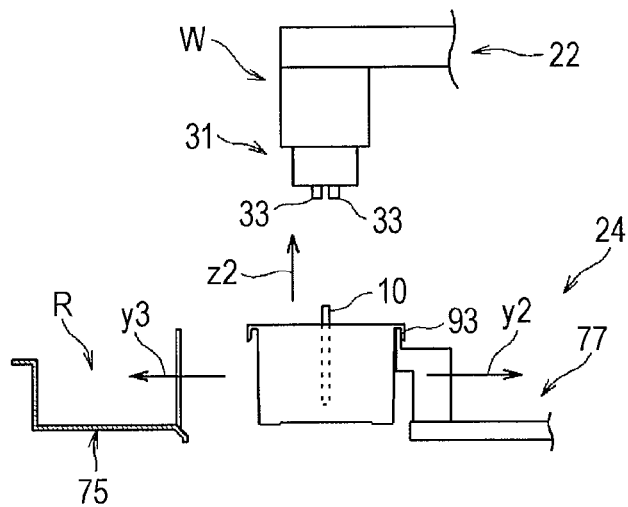

FIGS. 23A to 23C are schematic side views describing the operation of the longitudinal transport section 77 of the rack transport mechanism 24. In FIG. 23A, the rack 12 taken out from the take-out collecting position R of the accumulating section 75 is positioned on the back side than the specimen transfer position W by retreating the engagement nail 93 of the longitudinal transport section 77 to the initial position. As described above, when the vertical transport mechanism 22 takes out the specimen plate 10 performed with imaging from the transportation case 52 in the horizontal transport mechanism 23 (see FIG. 10B) and transports the same to the upper position H of the specimen transfer position W, the longitudinal transport section 77 of the rack transport mechanism 24 moves the rack 12 forward (arrow y1) and positions the same on the lower side of the gripping section 31.

Figure 12:
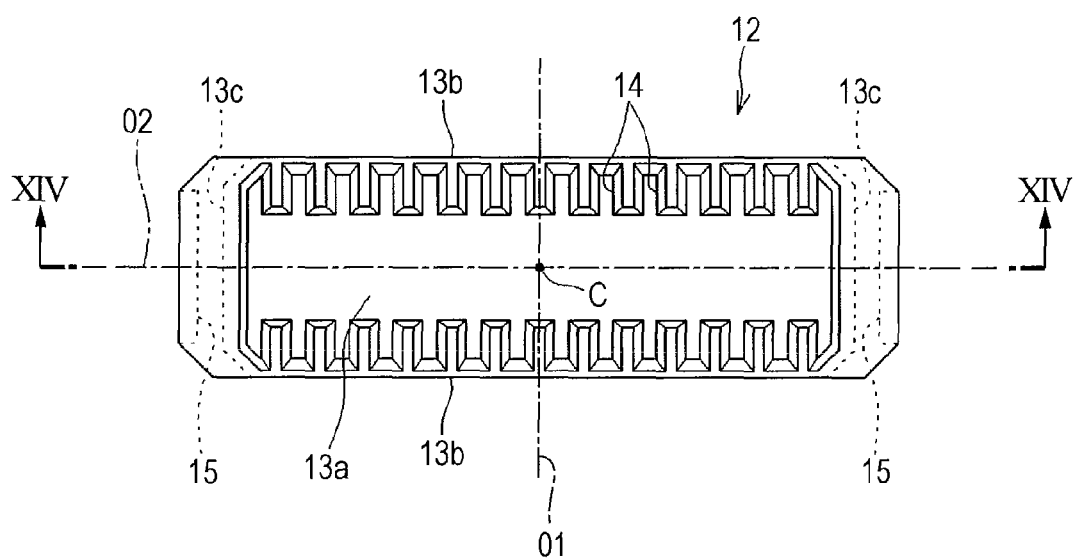
FIG. 12 is a plan view of the rack.

As shown in FIG. 12, the rack 12 includes a storage space of the specimen plate 10 at a plurality of areas in the front-back direction, so that the longitudinal transport section 77 moves the rack 12 forward to align a predetermined storage space, to which the specimen plate 10 is to be inserted, at the lower side of the specimen plate 10.

Then, as shown in FIG. 23B, the gripping section 31 in the vertical transport mechanism 22 is lowered and the specimen plate 10 is inserted into the rack 12.

Thereafter, as shown in FIG. 23C, the gripping section 31 is raised with the gripping nail 33 of the gripping section 31 opened. The rack 12 is moved toward the back side (arrow y2) by the longitudinal transport section 77 when successively storing the specimen plate 10 in the rack 12, and the rack 12 is further moved forward (arrow y3) by the longitudinal transport section 77 to return the rack 12 to the take-out collecting position R in the accumulating section 75 when the storing of the specimen plate 10 with respect to the rack 12 is finished.

As shown in FIG. 19C and FIG. 20A, when the rack 12 is returned to the accumulating section 75, a new empty rack 12 is taken out from the accumulating section 75 and the operations after FIG. 23A are again repeatedly carried out.

The rack transport mechanism 24 of the present embodiment sets a plurality of racks 12 so as to be lined in the left-right direction in the accumulating section 75 with the longitudinal direction of the rack 12 (direction in which the specimen plates 10 are lined) directed in the front-back direction, and transports the rack 12 in the left-right direction in the relevant accumulating section 75. Thus, the accumulating section 75 of the rack transport mechanism 24 can be configured small in the left-right direction and the transportation distance in the left-right direction of the rack 12 by the lateral transport section 76 can also be reduced compared to when the longitudinal direction of the rack 12 is directed in the left-right direction.

The rack transport mechanism 24 can perform the operation of taking out and collecting the rack 12 with respect to the accumulating section 75 and the operation of aligning each storage position of the rack 12 at the standby position of the specimen plate 10 with the movement in one direction since the direction of taking out and collecting the rack 12 with respect to the accumulating section 75 and the direction in which the specimen plates 10 are lined in the rack 12 are coincided, whereby the configuration of the rack transport mechanism 24 can be simplified.

Furthermore, the rack transport mechanism 24 transports the rack 12 in the front-back direction toward a specimen storage position with the opening directed toward the upper side, so that the specimen plate 10 is inserted from the upper side to the rack 12 by the vertical transport mechanism 22 at the specimen storage position. The transportation distance of the specimen plate 10 thus becomes as short as possible by transporting the rack 12 itself, and the liquid such as the immersion oil, and the like can be suppressed from leaking out to the transportation path of the specimen plate 10.

The specimen storage device 20 of the present embodiment includes the pre-stage accumulating section 75A for accumulating a rack 12 not stored with a specimen, and a post-stage accumulating section 75B for accumulating the rack 12 stored with an imaged specimen plate 10 on the front portion side of the specimen transporter 3 (front side than the specimen transport mechanisms 21 to 23), so that the user can supply the rack 12 to the pre-stage accumulating section 75A and take out the rack 12 from the post-stage accumulating section 75B at one area on the front side of the specimen transporter 3, whereby the operability of such operations can be enhanced.

If the rack 12 that is not stored with the specimen is accumulated in the pre-stage accumulating section 75, exchange with the rack 12 stored with the specimen can be rapidly carried, whereby the operation efficiency can be enhanced. Furthermore, since the rack 12 stored with the specimen can be temporarily accumulated by arranging the post-stage accumulating section 75B, the next rack 12 not stored with the specimen can be moved to the specimen storage position without taking the rack 12 out from the specimen transporter 3.

The specimen testing system 1 of the present embodiment has the specimen transporter 3 arranged between the specimen preparing apparatus 2 and the specimen imaging apparatus 4, and the specimen plate 10 prepared by the specimen preparing apparatus 2 is not directly supplied to the specimen imaging apparatus 4 but is supplied through the specimen transporter 3. Furthermore, the specimen plate 10 performed with imaging is not collected at the specimen imaging apparatus 4, but is collected to the rack 12 at the specimen transporter 3. Thus, the specimen imaging apparatus 4 does not need to include a structure for receiving the specimen plate 10 from the specimen preparing apparatus 2 and a structure for collecting the specimen plate 10 performed with imaging, and merely needs to include the transfer section 4e of the specimen with respect to transporter 3. The structure is thus simplified and miniaturized. Furthermore, since the specimen preparing apparatus 2 also does not need to include a structure for transporting the specimen plate 10 to the specimen imaging apparatus 4, the structure can be simplified and miniaturized.

Furthermore, the specimen transporter 3 has a function of transporting the specimen plate 10 from the specimen preparing apparatus 2 to the specimen imaging apparatus 4 and a function of collecting the specimen plate 10 performed with imaging in the specimen imaging apparatus 4, so that the system scale of the entire specimen testing system 1 can be reduced compared to when realizing such functions with separate apparatuses.

The specimen transporter 3 can collect the used cassette 11 and the specimen plate 10 performed with imaging, so that the user merely needs to take out and process the used cassette 11 and the specimen plate 10 performed with imaging only from the specimen transporter 3, whereby the operability of the processing can be enhanced.

In the specimen transporter 3 of the present embodiment, the transportation path from receiving the specimen plate 10 from the specimen preparing apparatus 2 up to transporting the specimen plate to the specimen imaging apparatus 4, and the transportation path from receiving the specimen plate 10 from the specimen imaging apparatus 4 up to storing the specimen plate in the rack 12 are partially overlapped. In other words, the vertical transport mechanism 22 and the horizontal transport mechanism 23 transport the specimen plate 10 on both transportation paths. The structure of the specimen transporter 3 can be simplified and miniaturized by partially overlapping both transportation paths and transporting the specimen plate 10 with the common specimen transport mechanisms 22, 23 on the overlapping transportation path.

The specimen transport mechanisms 21 to 23 in the specimen transporter 3 transport the specimen plate 10 while transferring the specimen plate 10 with each other at the specimen transfer position W. Thus, with the specimen transfer position W as a reference, smooth transportation of the specimen plate 10 cooperating with each other can be achieved. The vertical transport mechanism 22 linearly transports the specimen plate 10 in the up-down direction at the specimen transfer position W, so that the specimen plate 10 can be appropriately transferred with the cassette transport mechanism 21 and the horizontal transport mechanism 23 having different heights from each other. The vertical transport mechanism 22 also has a function of not only transferring the specimen plate 10 with the cassette transport mechanism 21 and the horizontal transport mechanism 23, but also storing the specimen plate 10 in the rack 12 transported by the rack transport mechanism 24, so that the specimen plate 10 can be appropriately transported between the horizontal transport mechanism 23 and the rack 12 having different heights from each other.

The present invention is not limited to the embodiment described above, and changes can be appropriately made within a scope of the invention described in the Claims.

For example, in the rack transport mechanism 24, the take-out collecting position R is set at one area in the accumulating section 75, but the take-out position and the collecting position may be individually provided. If the take-out position and the collecting position are individually provided, the stopper mechanism 78 may be arranged to both positions or the stopper mechanism 78 may be arranged to only one of the positions. The accumulating number of racks 12 in the accumulating section 75 also may be appropriately changed.

The supply of the specimen plate 10 to the specimen transporter 3 may be performed not only from the specimen preparing apparatus 2 but may also be performed by hand on the specimen receiving section 26.

The sample to be tested is not limited to blood and may be urine or samples collected from the uterine cervix.

The specimen imaging apparatus (specimen testing apparatus) 4 may not perform operations from imaging to analysis of the specimen, and may perform up to acquisition of the image data by imaging and perform the analysis of the image data with another device or by humans.

What is claimed is:

1. A specimen transporter connected to a specimen imaging apparatus, the specimen transporter comprising:
    a specimen receiving section configured to receive a specimen plate from a specimen preparing apparatus configured to prepare a specimen plate of a sample;
    a specimen transporting section configured to transport the specimen plate received by the specimen receiving section to the specimen imaging apparatus and transport the specimen plate imaged by the specimen imaging apparatus, and
    a specimen storage section configured to store the imaged specimen plate; wherein the specimen transporting section comprises:
    a specimen container configured to contain a specimen plate;
    a specimen container transport mechanism configured to transport the specimen container between a first position and a second position; and
    a specimen transport mechanism comprising a holder configured to hold and to release a specimen plate in the specimen container positioned at the first position and further comprising a vertical transport mechanism configured to transport the specimen plate only in a up-down position at the first position, wherein the specimen transporting section further includes a controller that is configured to:
    supply a specimen plate into the specimen container positioned at the first position by the specimen transport mechanism,
    transport the specimen container by the specimen container transport mechanism from the first position to the second position for providing the specimen plate to the specimen imaging apparatus to be imaged,
    receive the imaged specimen plate from the specimen imaging apparatus in the specimen container at the second position,
    transport the specimen container from the second position to the first position the specimen container transport mechanism,
    take out the imaged specimen plate from the specimen container at the first position by operation of the holder, and
    store the imaged specimen plate in the specimen storage section by operation of the holder.

2. The specimen transporter according to claim 1, wherein a transportation path of a specimen plate from the specimen receiving section to the specimen imaging apparatus and a transportation path of the specimen plate from the specimen imaging apparatus to the specimen storage section have a partially overlapped portion, and
    the specimen transport mechanism is located at the partially overlapped portion of the transportation paths.

3. The specimen transporter according to claim 1, wherein the specimen storage section comprises:
    a first accumulating section configured to accumulate a rack stored with an imaged specimen plate; and
    a second accumulating section configured to accumulate a rack not stored with a specimen plate,
    wherein the first accumulating section and the second accumulating section are on a front side of the specimen transporting section.

4. The specimen transporter according to claim 1, wherein the specimen receiving section is capable of receiving a plurality of specimen plates.

5. The specimen transporter according to claim 1, wherein the first position being on a transportation path of the specimen plate from the specimen receiving section to the specimen imaging apparatus and a transportation path of the specimen plate from the specimen imaging apparatus to the specimen storage section.

6. The specimen transporter according to claim 5, wherein the specimen transporting section comprises:
    a vertical transport mechanism configured to transport the specimen plate in an up-down direction at the first position;
    the second position proximate to the imaging apparatus for receiving the specimen plate from the specimen imaging apparatus and transferring the specimen plate to the specimen imaging apparatus, and
    wherein the vertical transport mechanism carries out receiving of the specimen plate from the specimen container and transferring the specimen plate to the specimen container, the specimen container being transported to the first position by the specimen container transport mechanism.

7. The specimen transporter according to claim 6, wherein the vertical transport mechanism is further configured to receive the specimen plate from the specimen container containing the imaged specimen plate that is transported to the first position by the specimen container transport mechanism.

8. The specimen transporter according to claim 1, wherein the specimen transporting section further comprises a rack transport mechanism configured to transport a rack for storing the imaged specimen plate between the first position and the specimen storage section,
    wherein a vertical transport mechanism transfers the imaged specimen plate, which is received from the specimen container, to the rack transported to the first position by the rack transport mechanism.

9. The specimen transporter according to claim 8, wherein the rack transport mechanism is further configured to transport the rack stored with the imaged specimen plate from the first position to the specimen storage section.

10. The specimen transporter according to claim 8, wherein: the vertical transport mechanism transports the holder holding the specimen plate to above the first position and then lowers the holder to store the specimen plate in the rack at the first position, and thereafter, releases the holder.

11. The specimen transporter according to claim 1, wherein the sample is blood; and the specimen preparing apparatus prepares a blood smear specimen plate.

12. A specimen imaging system comprising:
    a specimen preparing apparatus configured to prepare a specimen plate of a sample;
    a specimen imaging apparatus configured to image the specimen plate; and
    a specimen transporter configured to transport the specimen plate between the specimen preparing apparatus and the specimen imaging apparatus;
    a specimen receiving section configured to receive the specimen plate prepared by the specimen preparing apparatus;

a specimen storage section configured to store the specimen plate imaged by the specimen imaging apparatus; and the specimen transporter comprises:

a specimen transporting section configured to transport the specimen plate received by the specimen receiving section to the specimen imaging apparatus and transport the specimen plate imaged by the specimen imaging apparatus to the specimen storage section, wherein:

the specimen transporting section comprising;

a specimen container configured to contain a specimen plate;

a specimen container transport mechanism configured to transport the specimen container between a first position and a second position; and a specimen transport mechanism comprising a holder configured to hold and to release a specimen plate in the specimen container positioned at the first position and further comprising a vertical transport mechanism configured to transport the specimen plate only in a up-down position at the first position, wherein the specimen transporting section further includes a controller that is configured to:

supply a specimen plate into specimen container positioned at the first position by the specimen transport mechanism, transport the specimen container by the specimen container transport mechanism from the first position to the second position for providing the specimen plate to the specimen imaging apparatus to be imaged, receive the imaged specimen plate from the specimen imaging apparatus in the specimen container at the second position, transport the specimen container from the second position to the first position by the specimen container transport mechanism, take out the imaged specimen plate from the specimen container at the first position by operation of the holder, and store the imaged specimen plate in the specimen storage section by operation of the holder.

13. The specimen imaging system according to claim 12, wherein: the sample is blood; and the specimen preparing apparatus prepares a blood smear specimen plate.

14. The specimen imaging system according to claim 12, wherein a transportation path of a specimen plate from the specimen receiving section to the specimen imaging apparatus and a transportation path of the specimen plate from the specimen imaging apparatus to the specimen storage section have a partially overlapped portion, and the specimen transport mechanism is located at the partially overlapped portion of the transportation paths.

15. The specimen imaging system according to claim 12, wherein the specimen storage section comprises:

a first accumulating section configured to accumulate a rack stored with an imaged specimen plate; and a second accumulating section configured to accumulate a rack not stored with a specimen plate, wherein the first accumulating section and the second accumulating section are on a front side of the specimen transporting section.

16. The specimen imaging system according to claim 12, wherein: the specimen receiving section is capable of receiving a plurality of specimen plates.

17. The specimen imaging system according to claim 12, wherein the first position being on a transportation path of the specimen plate from the specimen receiving section to the specimen imaging apparatus and a transportation path of the specimen plate from the specimen imaging apparatus to the specimen storage section.

18. The specimen imaging system according to claim 17, wherein the specimen transporting section comprises:

a vertical transport mechanism configured to transport the specimen plate in an up-down direction at the first position;

the second position proximate to the imaging apparatus for carrying receiving of the specimen plate from the specimen imaging apparatus and transferring the specimen plate to the specimen imaging apparatus, and wherein the vertical transport mechanism carries out receiving of the specimen plate from the specimen container and giving of the specimen plate to the specimen container, the specimen container being transported to the first position by the specimen container transport mechanism.

* * * * *